United States Patent
Tsuyuki

(10) Patent No.: US 10,863,959 B2
(45) Date of Patent: Dec. 15, 2020

(54) X-RAY CT APPARATUS

(71) Applicant: Toshiba Medical Systems Corporation, Otawara (JP)

(72) Inventor: Masaharu Tsuyuki, Nasushiobara (JP)

(73) Assignee: Canon Medical Systems Corporation, Otawara (JP)

(*) Notice: Subject to any disclaimer, the term of this patent is extended or adjusted under 35 U.S.C. 154(b) by 737 days.

(21) Appl. No.: 15/438,256

(22) Filed: Feb. 21, 2017

(65) Prior Publication Data

US 2017/0172524 A1    Jun. 22, 2017

Related U.S. Application Data

(63) Continuation of application No. PCT/JP2016/088249, filed on Dec. 21, 2016.

(30) Foreign Application Priority Data

Dec. 21, 2015  (JP) ................................. 2015-248954

(51) Int. Cl.
*A61B 6/00* (2006.01)
*A61B 6/03* (2006.01)
(Continued)

(52) U.S. Cl.
CPC .............. *A61B 6/487* (2013.01); *A61B 6/032* (2013.01); *A61B 6/0407* (2013.01);
(Continued)

(58) Field of Classification Search
CPC ........... A61B 6/00; A61B 6/04; A61B 6/0407; A61B 6/0457; A61B 6/0492; A61B 6/08;
(Continued)

(56) References Cited

U.S. PATENT DOCUMENTS 5,304,806 A * 4/1994 Hines .................... G01T 1/1647
                                                        250/363.04
7,197,170 B2 * 3/2007 Dwyer .................. G06T 7/0012
                                                        382/128
(Continued)

FOREIGN PATENT DOCUMENTS

JP    7-236633 A    9/1995
JP    11-137543 A   5/1999
(Continued)

OTHER PUBLICATIONS

International Search Report dated Apr. 4, 2017 in PCT/JP2016/088249 (with English language translation).
Written Opinion dated Apr. 4, 2017 in PCT/JP2016/088249.

Primary Examiner — Anastasia Midkiff
(74) Attorney, Agent, or Firm — Oblon, McClelland, Maier & Neustadt, L.L.P.

(57) ABSTRACT

An X-ray CT apparatus includes: a gantry having an opening provided to be interposed between an X-ray tube and an X-ray detector; a couch including driving circuitry for inserting a couchtop on which a subject is placed, into the opening; storage circuitry storing therein pieces of information that are related to puncture positions of the couchtop and correspond to pieces of unique information of practitioners who each apply a manipulation to the subject; and processing circuitry configured, when a first practitioner is to apply the manipulation, to control the driving circuitry so as to move the couchtop to a puncture position indicated by a piece of information related to a puncture position corresponding to a piece of unique information pertaining to the first practitioner, the piece of information being among the pieces of information that are related to the puncture positions and stored in the storage circuitry.

11 Claims, 17 Drawing Sheets

(51) Int. Cl.
*A61B 6/04* (2006.01)
*A61B 34/00* (2016.01)
*A61B 34/20* (2016.01)
*A61B 6/08* (2006.01)
*A61B 34/10* (2016.01)

(52) U.S. Cl.
CPC ............ *A61B 6/4035* (2013.01); *A61B 6/467* (2013.01); *A61B 6/469* (2013.01); *A61B 6/486* (2013.01); *A61B 6/5205* (2013.01); *A61B 6/5294* (2013.01); *A61B 6/542* (2013.01); *A61B 34/20* (2016.02); *A61B 34/25* (2016.02); *A61B 6/08* (2013.01); *A61B 6/46* (2013.01); *A61B 6/465* (2013.01); *A61B 2034/102* (2016.02); *A61B 2034/2046* (2016.02); *A61B 2560/0266* (2013.01)

(58) Field of Classification Search
CPC ... A61B 6/46; A61B 6/461; A61B 6/463–465; A61B 6/467; A61B 6/469; A61B 6/48; A61B 6/486; A61B 6/487; A61B 6/52; A61B 6/5211; A61B 6/5217; A61B 6/5229; A61B 6/5297; A61B 2018/00988; A61B 34/10; A61B 34/20; A61B 34/25; A61B 90/08; A61B 90/36; A61B 90/37; A61B 2034/101; A61B 2034/102; A61B 2034/107; A61B 2034/108; A61B 2034/2046; A61B 2034/2051; A61B 2034/2055; A61B 2090/0804; A61B 2090/0805; A61B 2090/0807; A61B 2090/0811; A61B 2090/364; A61B 2090/368; A61B 2090/376; A61B 2560/0266; G06T 7/0012

See application file for complete search history.

(56) References Cited

U.S. PATENT DOCUMENTS

| | | | | |
|---|---|---|---|---|
| 2006/0258938 | A1* | 11/2006 | Hoffman | A61B 1/00193 600/424 |
| 2012/0201421 | A1* | 8/2012 | Hartmann | A61B 6/12 382/103 |
| 2013/0060146 | A1* | 3/2013 | Yang | A61B 5/055 600/476 |
| 2014/0055489 | A1* | 2/2014 | Itkowitz | G06T 11/40 345/633 |
| 2014/0072097 | A1 | 3/2014 | Mukumoto | |
| 2016/0374764 | A1* | 12/2016 | Kemp | A61B 34/20 600/424 |

FOREIGN PATENT DOCUMENTS

| | | |
|---|---|---|
| JP | 2002-34969 A | 2/2002 |
| JP | 2003-88518 A | 3/2003 |
| JP | 2003-126083 A | 5/2003 |
| JP | 2013-176540 A | 9/2013 |

* cited by examiner

FIG.4

|  | IN/OUT | UP/DOWN | LEFT/RIGHT |  |  |
|---|---|---|---|---|---|
| CURRENT POSITION | 10.0 | 30.0 | 0.0 |  |  |
| TARGET POSITION | ⌐40 | ⌐41 | ⌐42 | ⌐43 STORE TARGET POSITION | ⌐44 MOVE TO TARGET POSITION |
| OPERATION POSITION | ⌐50 | ⌐51 | ⌐52 | ⌐53 STORE OPERATION POSITION | ⌐54 MOVE TO OPERATION POSITION |

FIG.5

|  | IN/OUT | UP/DOWN | LEFT/RIGHT |  |  |
|---|---|---|---|---|---|
| CURRENT POSITION | 10.0 | 30.0 | 0.0 |  |  |
| TARGET POSITION | ⌐40 10.0 | ⌐41 30.0 | ⌐42 0.0 | ⌐43 STORE TARGET POSITION | ⌐44 MOVE TO TARGET POSITION |
| OPERATION POSITION | ⌐50 | ⌐51 | ⌐52 | ⌐53 STORE OPERATION POSITION | ⌐54 MOVE TO OPERATION POSITION |

| HEIGHT | WEIGHT | DOMINANT ARM | IN/OUT | UP/DOWN | LEFT/RIGHT |
|---|---|---|---|---|---|
| ⋮ | ⋮ | ⋮ | ⋮ | ⋮ | ⋮ |
| 175 | 55 | RIGHT | 130.0 | 20.0 | 40.0 |
| ⋮ | ⋮ | ⋮ | ⋮ | ⋮ | ⋮ |

FIG.14

| HEIGHT OF PRACTI-TIONER | WEIGHT OF PRACTI-TIONER | DOMINANT ARM OF PRACTI-TIONER | HEIGHT OF PATIENT | WEIGHT OF PATIENT | IN/OUT | UP/DOWN | LEFT/RIGHT |
|---|---|---|---|---|---|---|---|
| ⋮ | ⋮ | ⋮ | ⋮ | ⋮ | ⋮ | ⋮ | ⋮ |
| 175 | 55 | RIGHT | 165 | 55 | 135.0 | 20.0 | 45.0 |
| ⋮ | ⋮ | ⋮ | ⋮ | ⋮ | ⋮ | ⋮ | ⋮ |

FIG.15

| HEIGHT OF PRACTI-TIONER | WEIGHT OF PRACTI-TIONER | DOMINANT ARM OF PRACTI-TIONER | HEIGHT OF PATIENT | WEIGHT OF PATIENT | IN/OUT | UP/DOWN | LEFT/RIGHT |
|---|---|---|---|---|---|---|---|
| ⋮ | ⋮ | ⋮ | ⋮ | ⋮ | ⋮ | ⋮ | ⋮ |
| 175 | 55 | RIGHT | 160 | 50 | 105.0 | 60.0 | 25.0 |
| ⋮ | ⋮ | ⋮ | ⋮ | ⋮ | ⋮ | ⋮ | ⋮ |

FIG.22

| HEIGHT OF PRACTI- TIONER | WEIGHT OF PRACTI- TIONER | DOMINANT ARM OF PRACTI- TIONER | TARGET REGION | MANIPULA- TION | IN/ OUT | UP/ DOWN | LEFT/ RIGHT |
|---|---|---|---|---|---|---|---|
| : | : | : | : | : | : | : | : |
| 175 | 55 | RIGHT | CHEST | RFA | 180.0 | 70.0 | 60.0 |
| : | : | : | : | : | : | : | : |

FIG.23

| HEIGHT OF PRACTI- TIONER | WEIGHT OF PRACTI- TIONER | DOMINANT ARM OF PRACTI- TIONER | TARGET REGION | MANIPULA- TION | IN/ OUT | UP/ DOWN | LEFT/ RIGHT |
|---|---|---|---|---|---|---|---|
| : | : | : | : | : | : | : | : |
| 175 | 55 | RIGHT | FOOT | RFA | 130.0 | 50.0 | 80.0 |
| : | : | : | : | : | : | : | : |

| HEIGHT OF PRACTI-TIONER | WEIGHT OF PRACTI-TIONER | DOMINANT ARM OF PRACTI-TIONER | POSITION OF PRACTI-TIONER | IN/OUT | UP/DOWN | LEFT/RIGHT |
|---|---|---|---|---|---|---|
| ⋮ | ⋮ | ⋮ | ⋮ | ⋮ | ⋮ | ⋮ |
| 175 | 55 | RIGHT | RIGHT SIDE | 130.0 | 20.0 | 40.0 |
| ⋮ | ⋮ | ⋮ | ⋮ | ⋮ | ⋮ | ⋮ |

X-RAY CT APPARATUS

CROSS-REFERENCE TO RELATED APPLICATIONS

This application is a continuation of PCT international application Ser. No. PCT/JP2016/088249 filed on Dec. 21, 2016 which designates the United States, incorporated herein by reference, and which claims the benefit of priority from Japanese Patent Application No. 2015-248954, filed on Dec. 21, 2015, the entire contents of which are incorporated herein by reference.

FIELD

Embodiments described herein relate generally to an X-ray CT apparatus.

BACKGROUND

Conventionally, when an image taking process is performed by an X-ray Computed Tomography (CT) apparatus, a CT fluoroscopy process is implemented by which an X-ray CT image is generated and displayed in a substantially real-time manner. More specifically, in the CT fluoroscopy process, the X-ray CT image is generated and displayed in the real-time manner by decreasing the acquisition rate of projection data so as to shorten the time period required by an image reconstructing process. As a result, the X-ray CT apparatus is able to display, in a real-time manner, an X-ray CT image rendering a puncture target site and a puncture needle for a medical practitioner (hereinafter, "practitioner") such as a medical doctor who performs a puncture process.

In this situation, the X-ray CT apparatus displays, in the real-time manner, the X-ray CT image rendering the puncture target site and the puncture needle, by moving a couchtop on which an examined subject (hereinafter, "subject") is placed up to a position (which may be referred to as a "target position") where the puncture target site is to be imaged and taking an image of the puncture target site. Further, when the practitioner performs a puncture process in which, for example, the puncture needle is advanced to the puncture target site, the X-ray CT apparatus adjusts the positional relationship between the practitioner and the subject, by moving the couchtop on which the subject is placed, in one direction (the body axis direction of the subject) from the target position up to the position (which may be referred to as an operation position) where the puncture process is to be performed.

BRIEF DESCRIPTION OF THE DRAWINGS

FIG. 4 is a drawing illustrating an example of a setting screen;

FIG. 5 is a drawing for explaining an example of a process performed by a setting function according to the first embodiment;

FIG. 14 is a drawing illustrating an example of a data structure of a first operation position database according to a fourth embodiment;

FIG. 15 is a drawing illustrating an example of a data structure of a first target position database according to the fourth embodiment;

FIG. 22 is a drawing illustrating an example of a data structure of a second operation position database according to a fifth embodiment;

FIG. 23 is a drawing illustrating an example of a data structure of a second target position database according to the fifth embodiment;

DETAILED DESCRIPTION

An X-ray CT apparatus according to an embodiment includes a gantry, a couch, storage circuitry, and processing circuitry. The gantry has an opening provided to be interposed between an X-ray tube and an X-ray detector. The couch includes driving circuitry configured to insert a couchtop on which a subject is placed, into the opening. The storage circuitry is configured to store therein pieces of information that are related to a plurality of puncture positions of the couchtop and that correspond to pieces of unique information of a plurality of practitioners who each apply a manipulation to the subject. The processing circuitry is configured, when a first practitioner is to apply the manipulation, to control the driving circuitry so as to move the couchtop to a puncture position indicated by a piece of information related to a puncture position corresponding to a piece of unique information pertaining to the first practitioner, the piece of information being among the pieces of information that are related to the plurality of puncture positions and are stored in the storage circuitry.

Exemplary embodiments of an X-ray CT apparatus will be explained below, with reference to the accompanying drawings. Possible embodiments are not limited to the embodiments described below. Further, in principle, it is possible to implement any of the embodiments in combination.

First Embodiment

Figure 1:
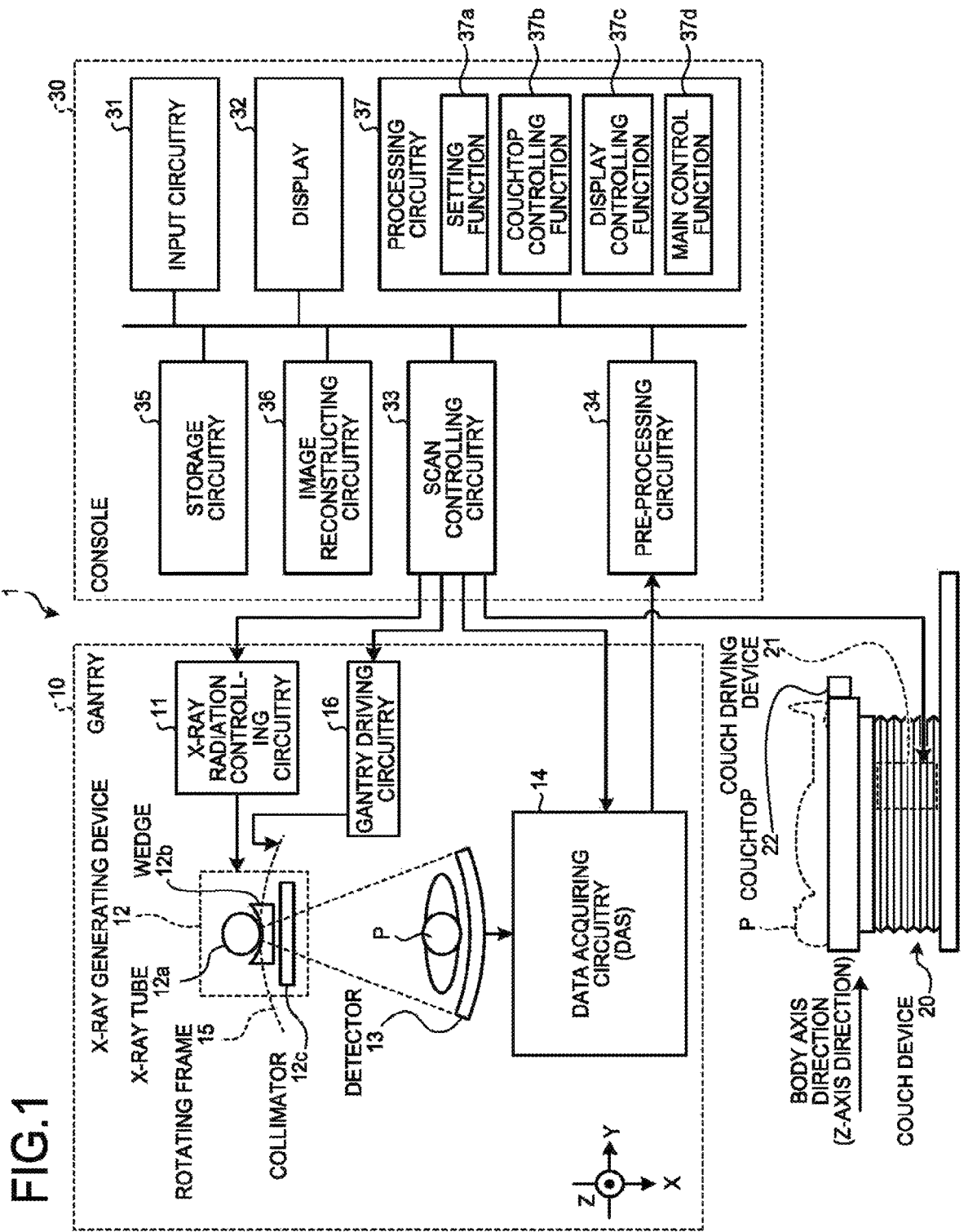
FIG. 1 is a functional block diagram illustrating a configuration of an X-ray CT apparatus according to an embodiment.

FIG. 1 is a diagram illustrating an example of a configuration of an X-ray CT apparatus according to a first embodiment. As illustrated in FIG. 1, an X-ray CT apparatus 1 according to the first embodiment includes a gantry 10, a couch device 20, and a console 30.

The gantry 10 is a device configured to radiate X-rays onto an examined subject (hereinafter, "subject") P, to detect X-rays that have passed through the subject P, and to output a detection result to the console 30. The gantry 10 has formed therein an opening that serves as an image taking space. The gantry 10 has an opening provided to be interposed between an X-ray tube (or an X-ray tube bulb; hereinafter, simply "X-ray tube") 12a (explained later) and a detector (an X-ray detector) 13 (explained later). The gantry 10 includes X-ray radiation controlling circuitry 11, an X-ray generating device 12, the detector 13, data acquiring circuitry (a Data Acquisition System [DAS]) 14, a rotating frame 15, and gantry driving circuitry 16.

The rotating frame 15 is an annular frame configured to support the X-ray generating device 12 and the detector 13 so as to oppose each other while the subject P is interposed therebetween and configured to be rotated by the gantry driving circuitry 16 (explained later) at a high speed on a circular orbit centered on the subject P.

The X-ray radiation controlling circuitry 11 is a device configured to control a high voltage supplied from a high-voltage generating unit (not illustrated) to the X-ray tube 12a. The X-ray tube 12a is configured to generate the X-rays by using the supplied high voltage. The X-ray radiation controlling circuitry 11 is configured to adjust the X-ray dose radiated onto the subject P, by adjusting the X-ray tube voltage and the X-ray tube current supplied to the X-ray tube 12a, under control of scan controlling circuitry 33 (explained later).

Further, the X-ray radiation controlling circuitry 11 is configured to perform a switching process on a wedge 12b. Further, by adjusting the opening degree of a collimator 12c, the X-ray radiation controlling circuitry 11 is configured to adjust the radiation range (a fan angle or a cone angle) of the X-rays. In the present embodiment, an arrangement is acceptable in which an operator manually switches among a plurality of types of wedges.

The X-ray generating device 12 is a device configured to generate the X-rays and to radiate the generated X-rays onto the subject P. The X-ray generating device 12 includes the X-ray tube 12a, the wedge 12b, and the collimator 12c.

The X-ray tube 12a is a vacuum tube configured to radiate an X-ray beam onto the subject P by using the high voltage supplied thereto by the high-voltage generating unit (not illustrated). The X-ray tube 12a radiates the X-ray beam onto the subject P, as the rotating frame 15 rotates. The X-ray tube 12a generates the X-ray beam that spreads with a fan angle or a cone angle. For example, under the control of the X-ray radiation controlling circuitry 11, the X-ray tube 12a is capable of continuously exposing X-rays in the entire surrounding of the subject P to realize a full reconstruction process and is capable of continuously exposing X-rays in an exposure range (180 degrees+a fan angle) that enables a half reconstruction to realize a half reconstruction process. Further, under the control of the X-ray radiation controlling circuitry 11, the X-ray tube 12a is capable of intermittently exposing X-rays (pulse X-rays) in positions (X-ray tube positions) set in advance. Further, the X-ray radiation controlling circuitry 11 is also capable of modulating the intensities of the X-rays exposed from the X-ray tube 12a. For example, the X-ray radiation controlling circuitry 11 increases the intensities of the X-rays exposed from the X-ray tube 12a in a specific X-ray tube position and decreases the intensities of the X-rays exposed from the X-ray tube 12a in a range other than the specific X-ray tube position.

The wedge 12b is an X-ray filter configured to adjust the X-ray dose of the X-rays exposed from the X-ray tube 12a. More specifically, the wedge 12b is a filter configured to pass and attenuate the X-rays exposed from the X-ray tube 12a, so that the X-rays radiated from the X-ray tube 12a onto the subject P have a predetermined distribution. For example, the wedge 12b is a filter obtained by processing aluminum so as to have a predetermined target angle and a predetermined thickness. The wedge may be referred to as a wedge filter or a bow-tie filter.

The collimator 12c is a slit configured to narrow down the radiation range of the X-rays of which the X-ray dose has been adjusted by the wedge 12b, under the control of the X-ray radiation controlling circuitry 11 (explained later).

The gantry driving circuitry 16 is configured to cause the X-ray generating device 12 and the detector 13 to revolve on the circular orbit centered on the subject P, by driving the rotating frame 15 to rotate.

The detector 13 a two-dimensional array detector (a planar detector) configured to detect the X-rays that have passed through the subject P. In the detector 13, a plurality of rows of detecting elements are arranged along the body axis direction of the subject P (i.e., the Z-axis direction in FIG. 1), while each row contains a plurality of X-ray detecting elements corresponding to a plurality of channels. More specifically, the detector 13 according to the first embodiment includes the X-ray detecting elements that are arranged in a large number of rows (e.g., 320 rows) along the body axis direction of the subject P. For example, the detector 13 is capable of detecting X-rays that have passed through the subject P in a wide range such as a range including the lungs or the heart of the subject P.

The data acquiring circuitry 14 is configured with the DAS and is configured to acquire projection data from X-ray detection data detected by the detector 13. For example, the data acquiring circuitry 14 generates the projection data by performing an amplifying process, an Analog/Digital (A/D) converting process, a sensitivity correcting process among the channels, and/or the like on X-ray intensity distribution data detected by the detector 13 and further transmits the generated projection data to the console 30 (explained later). For example, when X-rays are continuously exposed from the X-ray tube 12a while the rotating frame 15 is rotating, the data acquiring circuitry 14 acquires a group of projection data corresponding to the entire surrounding (corresponding to 360 degrees). Further, the data acquiring circuitry 14 transmits the acquired pieces of projection data to the console 30 (explained later), while keeping the pieces of projection data in correspondence with the X-ray tube positions. The X-ray tube positions serve as information indicating projection directions of the pieces of projection data. As additional information, the sensitivity correcting process among the channels may be performed by pre-processing circuitry 34 (explained later).

The couch device 20 is a device on which the subject P is placed and includes a couch driving device 21 and a couchtop 22. The couch driving device 21 is configured to move the subject P into the rotating frame 15 by moving the couchtop 22 in an X-axis direction, a Y-axis direction, and a Z-axis direction. The Z-axis is an axis extending along the insertion direction of the couchtop 22. The X-axis and the Y-axis are axes orthogonal to the Z-axis. The couchtop 22 is a board on which the subject P is placed. When an image taking process is to be performed on the subject P, the couchtop 22 having the subject P placed thereon is inserted into the opening formed in the gantry 10. In other words, the couch device 20 includes the couch driving device 21 configured to insert the couchtop 22 on which the subject P is placed, into the opening of the gantry 10. The couch device 20 is an example of a couch, whereas the couch driving device 21 is an example of driving circuitry.

For example, the gantry 10 performs a helical scan by which the subject P is helically scanned by causing the rotating frame 15 to rotate while the couchtop 22 is being moved. In another example, the gantry 10 performs a conventional scan by which the subject P is scanned on a circular orbit by causing the rotating frame 15 to rotate, while the position of the subject P is being fixed after the couchtop 22 is moved. In yet another example, the gantry 10 implements a step-and-shoot method by which the conventional scan is performed in multiple scan areas, by moving the position of the couchtop 22 at regular intervals.

The console 30 is a device configured to receive operations performed by the operator on the X-ray CT apparatus 1 and also configured to reconstruct X-ray CT image data by using the projection data acquired by the gantry 10. As illustrated in FIG. 1, the console 30 includes input circuitry 31, a display 32, the scan controlling circuitry 33, the pre-processing circuitry 34, storage circuitry 35, image reconstructing circuitry 36, and processing circuitry 37.

The input circuitry 31 includes a mouse, a keyboard, a trackball, a switch, a button (e.g., an exposure button), a joystick, and/or the like used by the operator of the X-ray CT apparatus 1 to input various types of instructions and various types of settings. The input circuitry 31 is configured to transfer information about the instructions and the settings received from the operator to the processing circuitry 37. For example, the input circuitry 31 receives, from the operator, an image taking condition for the X-ray CT image data, a reconstructing condition used when the X-ray CT image data is reconstructed, an image processing condition applied to the X-ray CT image data, and the like. Further, the input circuitry 31 receives an operation to select a medical examination to be performed on the subject. Further, the input circuitry 31 also receives a designation operation to designate a site in an image.

The display 32 is configured to display image data generated from the X-ray CT image data and to display a Graphical User Interface (GUI) used for receiving the various types of instructions and the various types of settings from the operator via the input circuitry 31, under control of the processing circuitry 37. Further, the display 32 is also configured to display a planning screen for a scanning plan, a screen during a scan, and the like.

Under the control of the processing circuitry 37, the scan controlling circuitry 33 is configured to control the projection data acquiring process performed by the gantry 10, by controlling operations of the X-ray radiation controlling circuitry 11, the gantry driving circuitry 16, the data acquiring circuitry 14, and the couch driving device 21. For example, the scan controlling circuitry 33 is configured to control projection data acquiring processes during an image taking process to acquire a position determining image (a scanogram image) and during a main image taking process (a main scan) to acquire an image used for a diagnosis purpose. In the present example, the X-ray CT apparatus 1 according to the first embodiment is configured so as to be able to take a two-dimensional scanogram image and a three-dimensional scanogram image. The scan controlling circuitry 33 is realized by using a processor, for example.

The pre-processing circuitry 34 is configured to generate corrected projection data by performing correcting processes such as a logarithmic converting process, an offset correcting process, a sensitivity correcting process, a beam hardening correcting process, and the like, on the projection data generated by the data acquiring circuitry 14. More specifically, the pre-processing circuitry 34 generates pieces of corrected projection data each for the projection data of the position determining image and for the projection data acquired by performing the main image taking process that were generated by the data acquiring circuitry 14 and further stores the pieces of corrected projection data into the storage circuitry 35. The pre-processing circuitry 34 is realized by using a processor, for example.

The storage circuitry 35 is configured to store therein the projection data generated by the pre-processing circuitry 34. More specifically, the storage circuitry 35 stores therein the projection data of the position determining image and the projection data for the diagnosis purpose acquired by performing the main image taking process that were generated by the pre-processing circuitry 34. Further, the storage circuitry 35 is configured to store therein image data generated by the image reconstructing circuitry 36 (explained later). Further, the storage circuitry 35 is configured to store therein a processing result obtained by the processing circuitry 37 (explained later), as appropriate. The storage circuitry 35 is realized by using, for example, a semiconductor memory device such as a Random Access Memory (RAM) or a flash memory, a hard disk, an optical disk, or the like.

The image reconstructing circuitry 36 is configured to reconstruct the X-ray CT image data by using the projection data stored in the storage circuitry 35. More specifically, the image reconstructing circuitry 36 reconstructs pieces of X-ray CT image data each from the projection data of the position determining image and the projection data of the image for the diagnosis purpose. In this situation, any of various methods can be used as the reconstructing method. For example, a back projection process may be used. Further, examples of the back projection process include a back projection process using a Filtered Back Projection (FBP) method. Alternatively, the image reconstructing circuitry 36 may reconstruct the X-ray CT image data by using a successive approximation method.

Further, the image reconstructing circuitry 36 is configured to generate image data by performing any of various types of image processing processes on the X-ray CT image data. After that, the image reconstructing circuitry 36 stores the reconstructed X-ray CT image data and the image data generated by performing any of the various types of image processing processes, into the storage circuitry 35. The image reconstructing circuitry 36 is realized by using a processor, for example.

The processing circuitry 37 is configured to exercise overall control of the X-ray CT apparatus 1 by controlling operations of the gantry 10, the couch device 20, and the console 30.

As illustrated in FIG. 1, the processing circuitry 37 is configured to execute a setting function 37a, a couchtop controlling function 37b, a display controlling function 37c, and a main control function 37d. Among these functions, the main control function 37d is configured to control a CT scan performed by the gantry 10, by controlling the scan controlling circuitry 33. Also, the main control function 37d is configured to control the image reconstructing process and the image generating process performed by the console 30, by controlling the image reconstructing circuitry 36. Further, the display controlling function 37c is configured to exercise control so that the display 32 displays various types of image data stored in the storage circuitry 35. In this situation, for example, the constituent elements of the processing circuitry 37 illustrated in FIG. 1, namely the functions such as the setting function 37a, the couchtop controlling function 37b, the display controlling function 37c, and the main control function 37d are recorded in the storage circuitry 35 in the form of computer-executable programs. The processing circuitry 37 is a processor configured to realize the functions corresponding to the computer programs (hereinafter, "programs"), by reading the programs from the storage circuitry 35 and executing the read programs. In other words, the processing circuitry 37 that has read the programs has the functions illustrated within the processing circuitry 37 in FIG. 1. FIG. 1 illustrates the example in which the single processing circuitry realizes the processing functions implemented by the setting function 37a, the couchtop controlling function 37b, the display controlling function 37c, and the main control function 37d; however, another arrangement is also acceptable in which a processing circuitry is structured by combining together a plurality of independent processors, so that the functions are realized as a result of the processors executing the programs.

The term "processor" used in the explanation above denotes, for example, circuitry such as a Central Processing Unit (CPU), a Graphics Processing Unit (GPU), an Application Specific Integrated Circuit (ASIC), a programmable logic device (e.g., a Simple Programmable Logic Device [SPLD], a Complex Programmable Logic Device [CPLD]), or a Field Programmable Gate Array (FPGA). Each of the processors realizes the function thereof by reading a program stored in the storage circuitry and executing the read program. Alternatively, it is also acceptable to directly incorporate the program into the circuitry of each of the processors, instead of having the programs stored in the storage circuitry. In that situation, each of the processors realizes the function thereof by reading the program incorporated in the circuitry thereof and executing the read program. The processors according to the present embodiment each do not necessarily have to be configured as a single circuitry. It is also acceptable to structure a single processor by combining together a plurality of independent circuitrys so as to realize the functions thereof.

Figure 2:
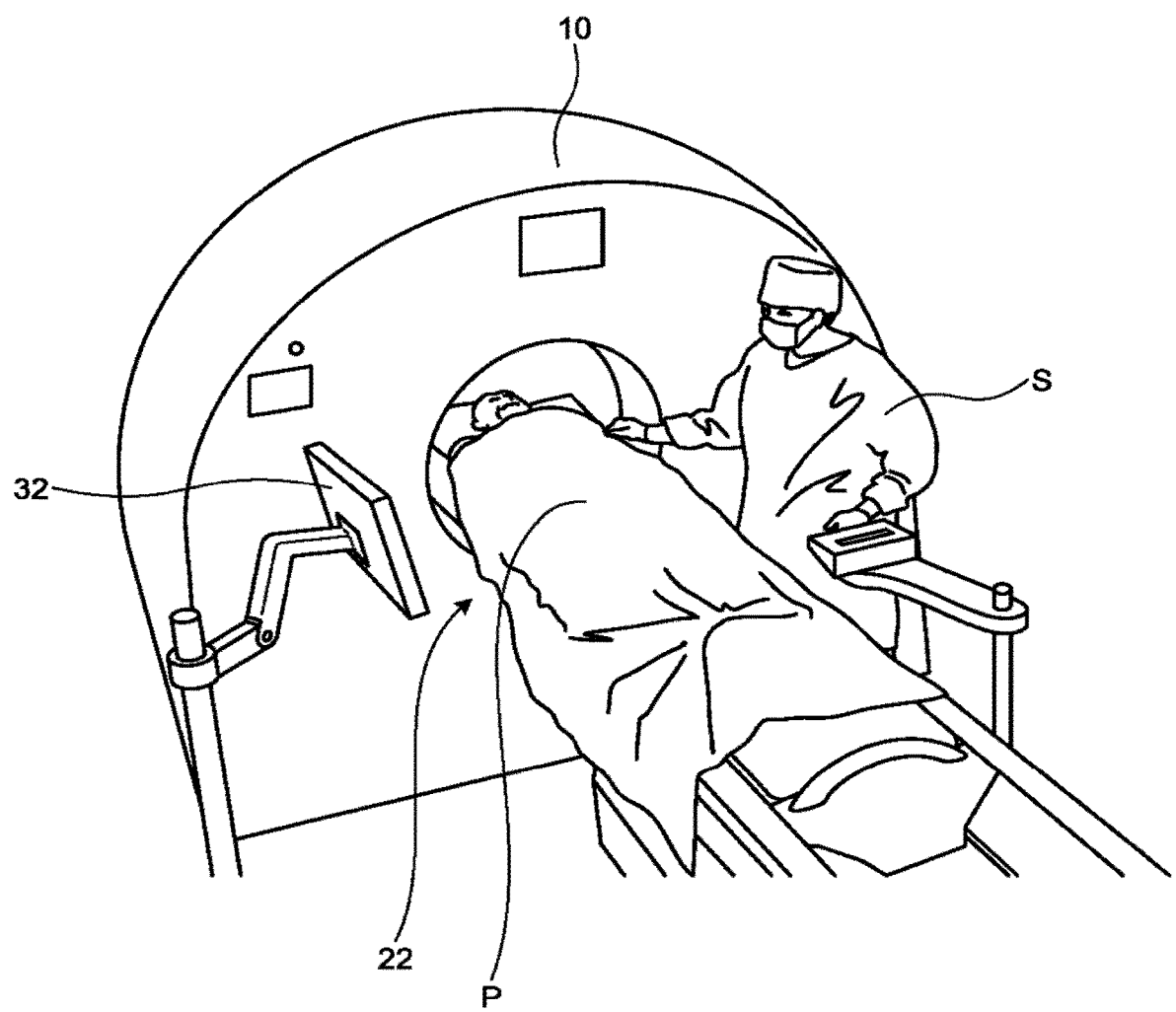
FIG. 2 is a drawing illustrating an example of a positional relationship among a subject P, a gantry, a couchtop, and a practitioner according to a first embodiment.

An overall configuration of the X-ray CT apparatus 1 according to the first embodiment has thus been explained. FIG. 2 is a drawing illustrating an example of a positional relationship among the subject P, the gantry 10, the couchtop 22, and a practitioner S according to the first embodiment. In the first embodiment, as illustrated by the example in FIG. 2, the practitioner S moves the couchtop 22 on which the subject P is placed, to an appropriate position and performs a puncture process by advancing a puncture needle, or the like. For example, the practitioner S moves the couchtop 22 to a position where he/she is able to easily operate the puncture needle such as a position where the practitioner S is not in contact with the gantry 10 and he/she is able to easily apply a force to the subject P, while viewing an X-ray CT image rendering a puncture target site and the puncture needle and being displayed on the display 32 in a real-time manner. The X-ray CT apparatus 1 structured as described above is configured, as explained below, so as to be able to move the subject to a position where the practitioner is able to easily perform the puncture process.

Next, processing functions of the setting function 37a and the couchtop controlling function 37b implemented by the processing circuitry 37 illustrated in FIG. 1 will be explained.

Figure 3:
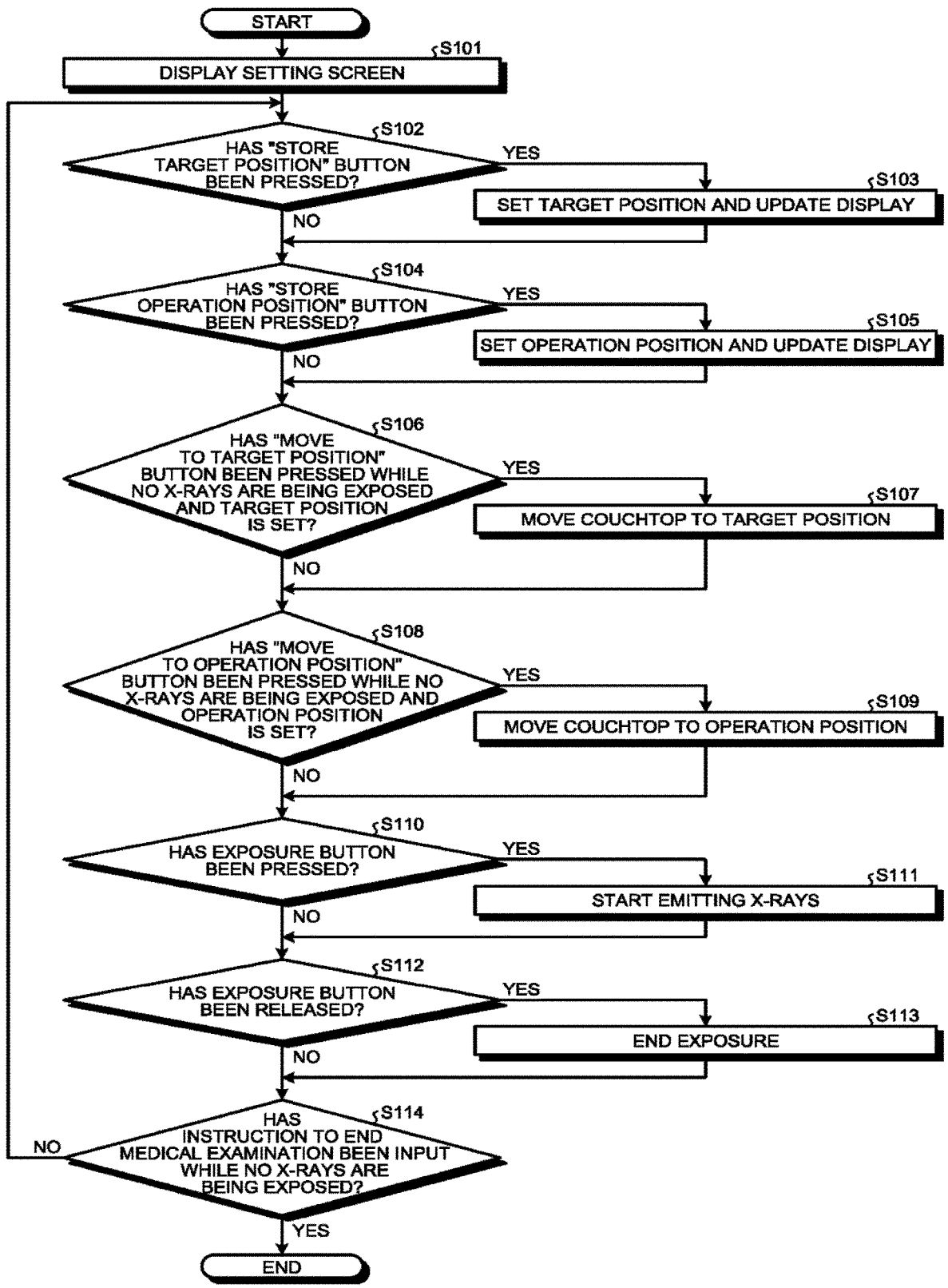
FIG. 3 is a flowchart illustrating an example of a flow in a process performed by an X-ray CT apparatus according to the first embodiment.

FIG. 3 is a flowchart illustrating an example of a flow in a process performed by the X-ray CT apparatus according to the first embodiment.

As illustrated by the example in FIG. 3, the setting function 37a causes the display 32 to display a setting screen used for setting an operation position that is a position of the couchtop 22 corresponding to when a practitioner performs a puncture process (step S101). FIG. 4 is a drawing illustrating an example of the setting screen. As illustrated in FIG. 4, a setting screen 60 contains the current position of the couchtop 22. In the example in FIG. 4, the current position (10.0, 30.0, 0.0) of the couchtop 22 is contained in the setting screen 60. In this situation, the current position (10.0, 30.0, 0.0) of the couchtop 22=(In/Out,Up/Down,Lef/Right)=(Z,X,Y) is satisfied.

Further, the setting screen 60 has a region 40 in which the Z-axis value of a target position having been set is displayed, a region 41 in which the X-axis value thereof is displayed, and a region 42 in which the Y-axis value thereof is displayed, when the target position that is a position of the couchtop 22 where a puncture target site (which may simply be referred to as a "target") is to be imaged has been set. Further, the setting screen 60 has a button used for storing and setting the target position (a "store target position" button) 43 and a button used for moving the couchtop 22 to the set target position (a "move to target position" button) 44.

Further, the setting screen 60 has a region 50 in which the Z-axis value of an operation position having been set is displayed, a region 51 in which the X-axis value thereof is displayed, and a region 52 in which the Y-axis value thereof is displayed, when the operation position has been set. Further, the setting screen 60 also has a button used for storing and setting the operation position (a "store operation position" button) 53 and a button used for moving the couchtop 22 to the set operation position (a "move to operation position" button) 54.

Returning to the description of FIG. 3, the setting function 37a judges whether or not the "store target position" button 43 has been pressed by the user via the input circuitry 31 (step S102). When the "store target position" button 43 has not been pressed (step S102: No), the setting function 37a proceeds to step S104 (explained later).

On the contrary, when the "store target position" button 43 has been pressed (step S102: Yes), the setting function 37a stores and sets the current position of the couchtop 22 into the storage circuitry 35 as a target position and further updates the displays of the regions 40 to 42 (step S103). FIG. 5 is a drawing for explaining an example of a process performed by the setting function according to the first embodiment. For example, when the "store target position" button 43 has been pressed on the setting screen 60 illustrated by the example in FIG. 4, the setting function 37a stores the current position of the couchtop 22 into the storage circuitry 35 as a target position so as to set the target position. After that, as illustrated by the example in FIG. 5, the setting function 37a causes the Z-axis value "10.0" of the set target position to be displayed in the region 40, causes the X-axis value "30.0" thereof to be displayed in the region 41, and causes the Y-axis value "0.0" thereof to be displayed in the region 42.

Returning to the description of FIG. 3, the setting function 37a judges whether or not the "store operation position" button 53 has been pressed by the user via the input circuitry 31 (step S104). When the "store operation position" button 53 has not been pressed (step S104: No), the setting function 37a proceeds to step S106 (explained later).

Figure 6:
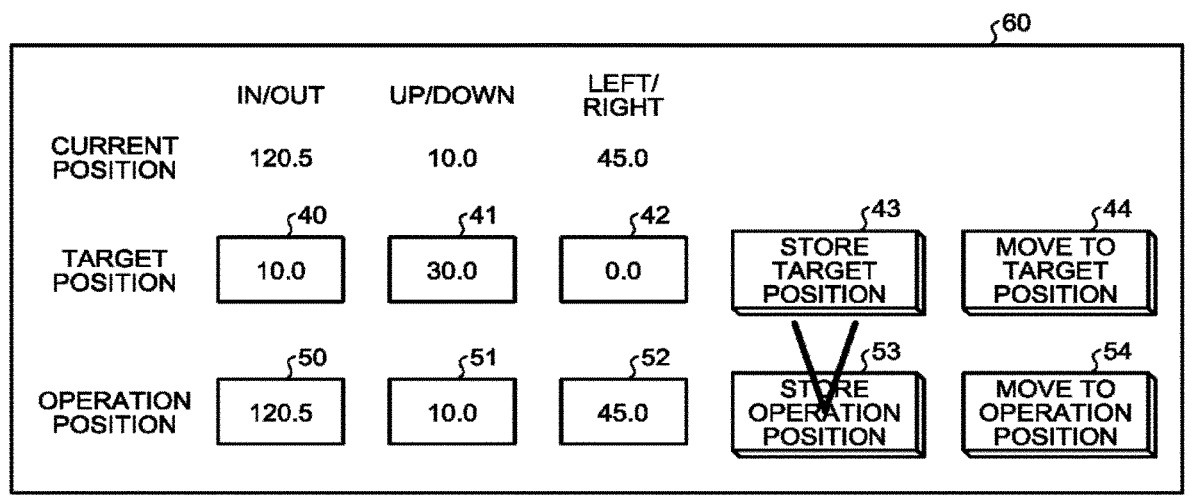
FIG. 6 is another drawing for explaining the example of the process performed by the setting function according to the first embodiment.

On the contrary, when the "store operation position" button 53 has been pressed (step S104: Yes), the setting function 37a stores and sets the current position of the couchtop 22 into the storage circuitry 35 as an operation position and further updates the displays of the regions 50 to 52 (step S105). FIG. 6 is another drawing for explaining the example of the process performed by the setting function according to the first embodiment. For example, when the "store operation position" button 53 has been pressed on the setting screen 60 illustrated by the example in FIG. 6, the setting function 37a stores the current position of the couchtop 22 into the storage circuitry 35 as an operation position so as to set the operation position. After that, as illustrated by the example in FIG. 6, the setting function 37a causes the Z-axis value "120.5" of the set operation position to be displayed in the region 50, causes the X-axis value "10.0" thereof to be displayed in the region 51, and causes the Y-axis value "45.0" thereof to be displayed in the region 52.

Returning to the description of FIG. 3, the couchtop controlling function 37b judges whether or not the "move to target position" button 44 has been pressed by the practitioner via the input circuitry 31 while the X-ray tube 12a is exposing no X-rays onto the subject P, and also, a target position is set (step S106). When the "move to target position" button 44 has not been pressed (step S106: No), the couchtop controlling function 37b proceeds to step S108 (explained later).

On the contrary, when the "move to target position" button 44 has been pressed (step S106: Yes), the couchtop controlling function 37b transmits an instruction to move the couchtop 22 to the set target position, to the scan controlling circuitry 33 (step S107). When having received the instruction, the scan controlling circuitry 33 controls the couch driving device 21 so as to move the couchtop 22 to the target position. Thus, the couch driving device 21 moves the couchtop 22 to the target position. Accordingly, by performing the simple operation of pressing the "move to target position" button 44, the practitioner is able to easily move the couchtop 22 to the target position.

After that, the couchtop controlling function 37b judges whether or not the "move to operation position" button 54 has been pressed by the practitioner via the input circuitry 31, while the X-ray tube 12a is exposing no X-rays onto the subject P, and also, the operation position is set (step S108). When the "move to operation position" button 54 has not been pressed (step S108: No), the couchtop controlling function 37b proceeds to step S110 (explained later).

On the contrary, when the "move to operation position" button 54 has been pressed (step S108: Yes), the couchtop controlling function 37b transmits an instruction to move the couchtop 22 to the set operation position, to the scan controlling circuitry 33 (step S109). Thus, the couchtop 22 is moved to the set operation position. Accordingly, by performing the simple operation of pressing the "move to operation position" button 54, the practitioner is able to easily move the couchtop 22 to the operation position.

After that, the main control function 37d judges whether or not the exposure button has been pressed (step S110). When the exposure button has not been pressed (step S110: No), the main control function 37d proceeds to step S112 (explained later).

On the contrary, when the exposure button has been pressed (step S110: Yes), the main control function 37d controls the scan controlling circuitry 33 so that the X-ray tube 12a starts exposing X-rays onto the subject P (step S111). Having received the control command, the scan controlling circuitry 33 controls the X-ray radiation controlling circuitry 11, the gantry driving circuitry 16, the data acquiring circuitry 14, and the couch driving device 21, so that the X-ray tube 12a starts exposing X-rays onto the subject P. As a result, the exposure of the X-rays is started, and a CT fluoroscopy process to generate and display an X-ray CT image in a substantially real-time manner, for example, is started. By performing the CT fluoroscopy process, the practitioner is able to check the position of the puncture target site, or the like. In this situation, while the exposure button is being pressed, the X-ray tube 12a keeps exposing X-rays onto the subject P.

After that, the main control function 37d judges whether or not the exposure button has been released (step S112). When the exposure button has not been released (step S112: No), the main control function 37d proceeds to step S114 (explained later).

On the contrary, when the exposure button has been released (step S112: Yes), the main control function 37d controls the scan controlling circuitry 33 so that the X-ray tube 12a finishes exposing the X-rays onto the subject P (step S113). When having received the control command, the scan controlling circuitry 33 controls the X-ray radiation controlling circuitry 11, the gantry driving circuitry 16, the data acquiring circuitry 14, and the couch driving device 21 so that the X-ray tube 12a finishes exposing the X-rays onto the subject P. Thus, the exposure of the X-rays is ended, and for example, the CT fluoroscopy process is ended.

After that, the main control function 37d judges whether or not an instruction to end the medical examination has been received from the practitioner via the input circuitry 31, while the X-ray tube 12a is exposing no X-rays onto the subject P (step S114). When no such instruction is received (step S114: No), the main control function 37d returns to step S101 described above. On the contrary, having received such an instruction (step S114: Yes), the main control function 37d ends the process.

The processes at steps S101 through S105 are steps corresponding to the setting function 37a. The processes at steps S101 through S105 are steps at which the setting function 37a is realized as a result of the processing circuitry 37 reading and executing a predetermined program corresponding to the setting function 37a from the storage circuitry 35. The processes at steps S106 through S109 are steps corresponding to the couchtop controlling function 37b. The processes at steps S106 through S109 are steps at which the couchtop controlling function 37b is realized as a result of the processing circuitry 37 reading and executing a predetermined program corresponding to the couchtop controlling function 37b from the storage circuitry 35. Further, the processes at steps S110 through S114 are steps corresponding to the main control function 37d. The processes at steps S110 through S114 are steps at which the main control function 37d is realized as a result of the processing circuitry 37 reading and executing a predetermined program corresponding to the main control function 37d from the storage circuitry 35.

Figure 7:
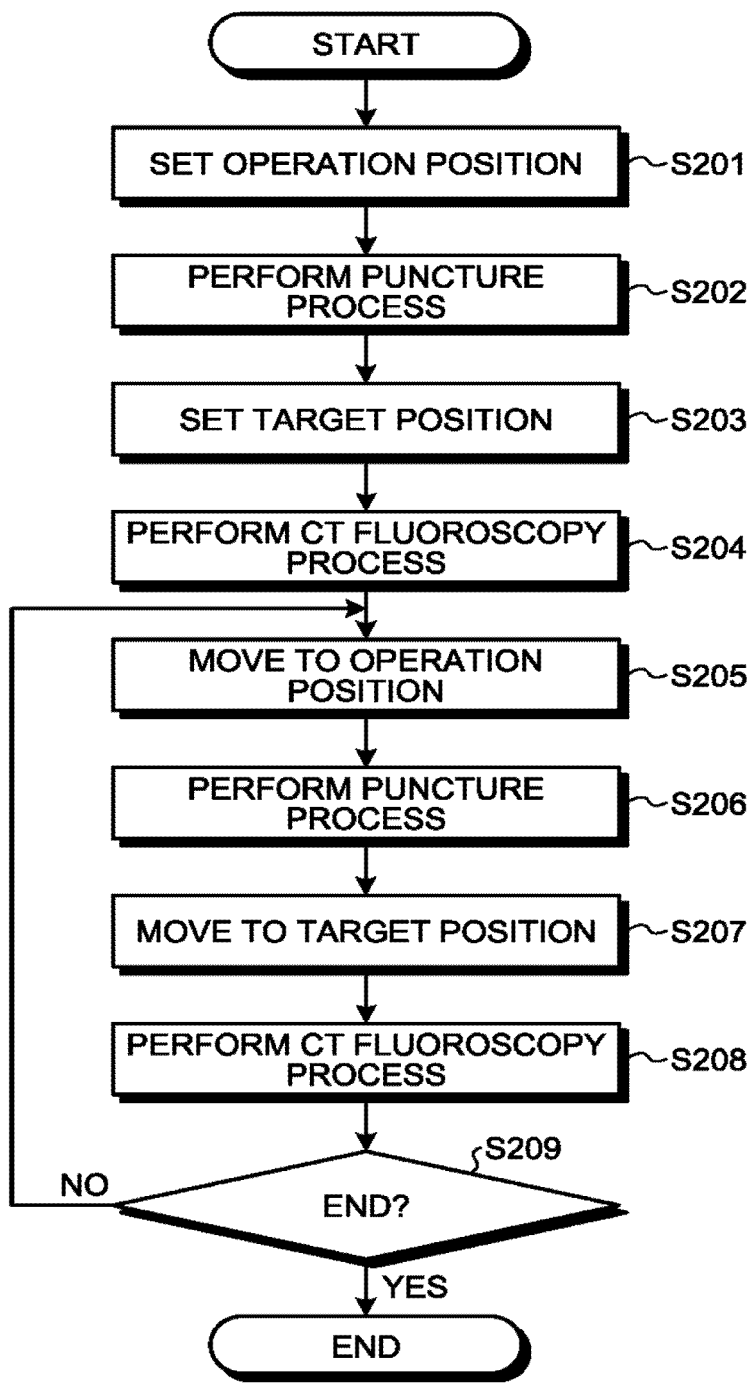
FIG. 7 is a flowchart illustrating an example of a flow in a medical examination according to the first embodiment.

Next, a flow in a medical examination to perform a puncture process will be explained. FIG. 7 is a flowchart illustrating an example of a flow in a medical examination according to the first embodiment. At step S201 in the example in FIG. 7, to perform a puncture process, the practitioner at first designates a position of the couchtop 22 via the input circuitry 31. Having received the designated position, the couchtop controlling function 37b controls the scan controlling circuitry 33 so as to move the couchtop 22 to the designated position. Having received the control command from the couchtop controlling function 37b, the scan controlling circuitry 33 moves the couchtop 22 to the designated position. After that, at step S201, when the current position of the couchtop 22 that has been moved to the designated position is considered to be a position where the practitioner S is able to easily operate a puncture needle, the practitioner S presses the "store operation position" button 53. As a result, the setting function 37a stores and sets the current position of the couchtop 22 into the storage circuitry 35 as an operation position.

On the contrary, at step S201, when the current position of the couchtop 22 that has been moved to the designated position is not considered to be a position where the practitioner S is able to easily operate the puncture needle, the practitioner S designates a position where he/she is able to easily operate the puncture needle via the input circuitry 31, so as to move the couchtop 22 to the designated position. After that, the practitioner presses the "store operation position" button 53.

In the manner described above, the setting function 37a stores and sets the position of the couchtop 22 used when the practitioner performs the puncture process, into the storage circuitry 35 as the operation position.

In other words, the X-ray CT apparatus 1 according to the first embodiment is configured so that the setting function 37a causes the display 32 to display the setting screen 60 used for receiving the instruction (the save instruction) to save the position of the couchtop 22 from the practitioner and stores the position of the couchtop 22 observed when the save instruction is received, into the storage circuitry 35.

In this situation, even when the practitioner is an expert in puncture processes, it would be difficult to set values on the Z-, X-, and Y-axes of the couchtop 22 as an operation position. In contrast, according to the first embodiment, the practitioner is able to actually move the couchtop 22 and to set the position where he/she is able to easily perform the puncture process as the operation position. Consequently, the configuration enables the practitioner to easily set the operation position where he/she is able to easily perform the puncture process.

After that, the practitioner performs the puncture process on the subject P after the couchtop 22 has been moved to the operation position (step S202).

Subsequently, at step S203, the practitioner designates, via the input circuitry 31, a target position that is the position of the couchtop 22 where a CT fluoroscopy process is to be performed. For example, the practitioner designates the target position in such a manner that a puncture target site is positioned on a scan surface. Accordingly, the couchtop controlling function 37b transmits an instruction to move the couchtop 22 to the designated target position, to the scan controlling circuitry 33. After that, when having received the instruction, the scan controlling circuitry 33 controls the couch driving device 21 so as to move the couchtop 22 to the designated target position. Accordingly, the couch driving device 21 moves the couchtop 22 to the target position. Subsequently, at step S203, the practitioner presses the "store target position" button 43. As a result, the setting function 37a stores and sets the current position of the couchtop 22 into the storage circuitry 35, as a target position.

After that, the practitioner starts an exposure of X-rays by pressing the exposure button (step S204). Accordingly, for example, a CT fluoroscopy process is started. In this situation, by performing the CT fluoroscopy process, the practitioner is able to check the position of the puncture target site, or the like. While the exposure button is being pressed, the X-ray tube 12a keeps exposing X-rays onto the subject P.

Subsequently, the practitioner ends the exposure of the X-rays by releasing the exposure button and also presses the "move to operation position" button 54 (step S205). As a result, the couchtop 22 is moved to the operation position set at step S201. In this situation, the operation position is a three-dimensional position expressed on the three axes including the X-axis and the Y-axis in addition to the Z-axis. In other words, possible positions of the operation position include positions along the insertion direction of the couchtop 22 as well as positions along the two directions orthogonal to the insertion direction. For this reason, the practitioner is able to move the subject P to a position where the puncture process is easily performed, with a degree of freedom higher than, for example, when the operation position is designated only in the Z-axis direction. Alternatively, the operation position may be a two- or more dimensional position expressed on at least one selected from between the X-axis and the Y-axis in addition to the Z-axis. In other words, possible positions of the operation position may include positions along the insertion direction of the couchtop 22 and positions along at least one direction orthogonal to the insertion direction.

Further, after the couchtop 22 is pulled out of the gantry 10, the degree of freedom of the couchtop 22 becomes higher. Thus, also in this regard, it is considered possible to bring the couchtop 22 to a position where the practitioner is able to easily perform the puncture process.

Subsequently, the practitioner performs the puncture process on the subject P after the couchtop 22 has been moved to the operation position (step S206).

After that, the practitioner presses the "move to target position" button 44 (step S207). As a result, the couchtop 22 is moved to the target position set at step S203.

Subsequently, the practitioner starts an exposure of X-rays by pressing the exposure button (step S208). Accordingly, for example, a CT fluoroscopy process is started.

After that, when the practitioner wishes to end the medical examination including the puncture process (step S209: Yes), the practitioner ends the medical examination. On the contrary, when the practitioner wishes to continue the medical examination (step S209: No), the process returns to step S205 described above.

The X-ray CT apparatus 1 according to the first embodiment has thus been explained. As explained above, the X-ray CT apparatus 1 is able to move the subject P to the position where the practitioner is able to easily perform the puncture process.

A First Modification Example of the First Embodiment

Figure 8:
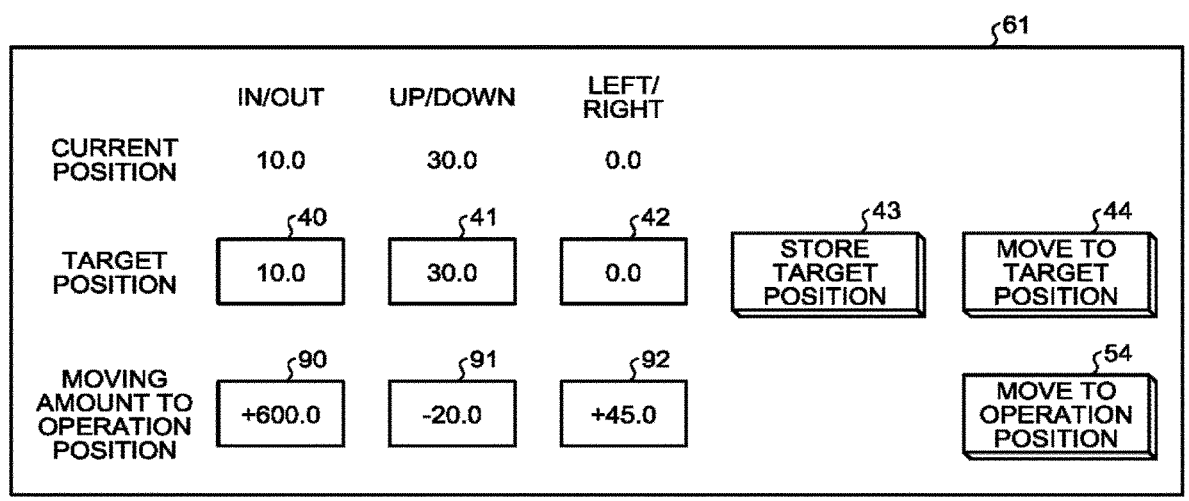
FIG. 8 is a drawing illustrating an example of a setting screen according to a modification example of the first embodiment.

In the first embodiment, the example is explained in which the operation position set by the practitioner is an absolute position. However, another arrangement is acceptable in which the practitioner inputs, on a setting screen, a moving amount to the operation position while using the target position as a reference. Thus, this embodiment will be explained as a first modification example of the first embodiment. Some of the elements of the configuration that are the same as those in the first embodiment will be referred to by using the same reference characters, and the explanation thereof will be omitted. FIG. 8 is a drawing illustrating an example of a setting screen according to the first modification example of the first embodiment. The setting function 37a causes the display 32 to display a setting screen 61 illustrated in FIG. 8.

The setting screen 61 has a region 90, a region 91, and a region 92. In the region 90, the practitioner inputs a moving amount to the Z-axis value of an operation position, while using the Z-axis value of the set target position as a reference. In the region 91, the practitioner inputs a moving amount to the X-axis value of the operation position, while using the X-axis value of the set target position as a reference. In the region 92, the practitioner inputs a moving amount to the Y-axis value of the operation position, while using the Y-axis value of the set target position as a reference. By inputting the moving amounts into the regions 90, 91, and 92 via the input circuitry 31, the practitioner sets the position relative to the target position, as the operation position.

FIG. 8 illustrates an example in which the moving amount from the Z-axis value of the set target position to the Z-axis value of the operation position is 600.0 mm in the positive direction on the Z-axis. Further, in the example in FIG. 8, the moving amount from the X-axis value of the set target position to the X-axis value of the operation position is 20.0 mm in the negative direction on the X-axis. Further, in the example in FIG. 6, the moving amount from the Y-axis value of the set target position to the Y-axis value of the operation position is 45.0 mm in the positive direction on the Y-axis.

The first modification example of the first embodiment has thus been explained. According to the first modification example, it is possible to move the subject P to the position where the practitioner is able to easily perform the puncture process, similarly to the first embodiment.

A Second Modification Example of the First Embodiment

Next, a second modification example of the first embodiment will be explained. By operating the input circuitry 31, the practitioner may input, on the setting screen 60, position information indicating a position of the couchtop 22, as an operation position. For example, on the setting screen 60, the practitioner may input a Z-axis value into the region 50, an X-axis value into the region 51, and a Y-axis value into the region 52. In that situation, when the practitioner inputs an instruction to set the operation position by operating the input circuitry 31, the setting function 37a stores and sets the Z-axis value, the X-axis value, and the Y-axis value that were input, into the storage circuitry 35, as the operation position. In other words, the setting function 37a is configured so that the display 32 is caused to display the setting screen 60 used for receiving the position information indicating the position of the couchtop 22 from the practitioner and so that the position of the couchtop 22 based on the received position information is stored and set into the storage circuitry 35 as the operation position.

Second Embodiment

Figure 9:
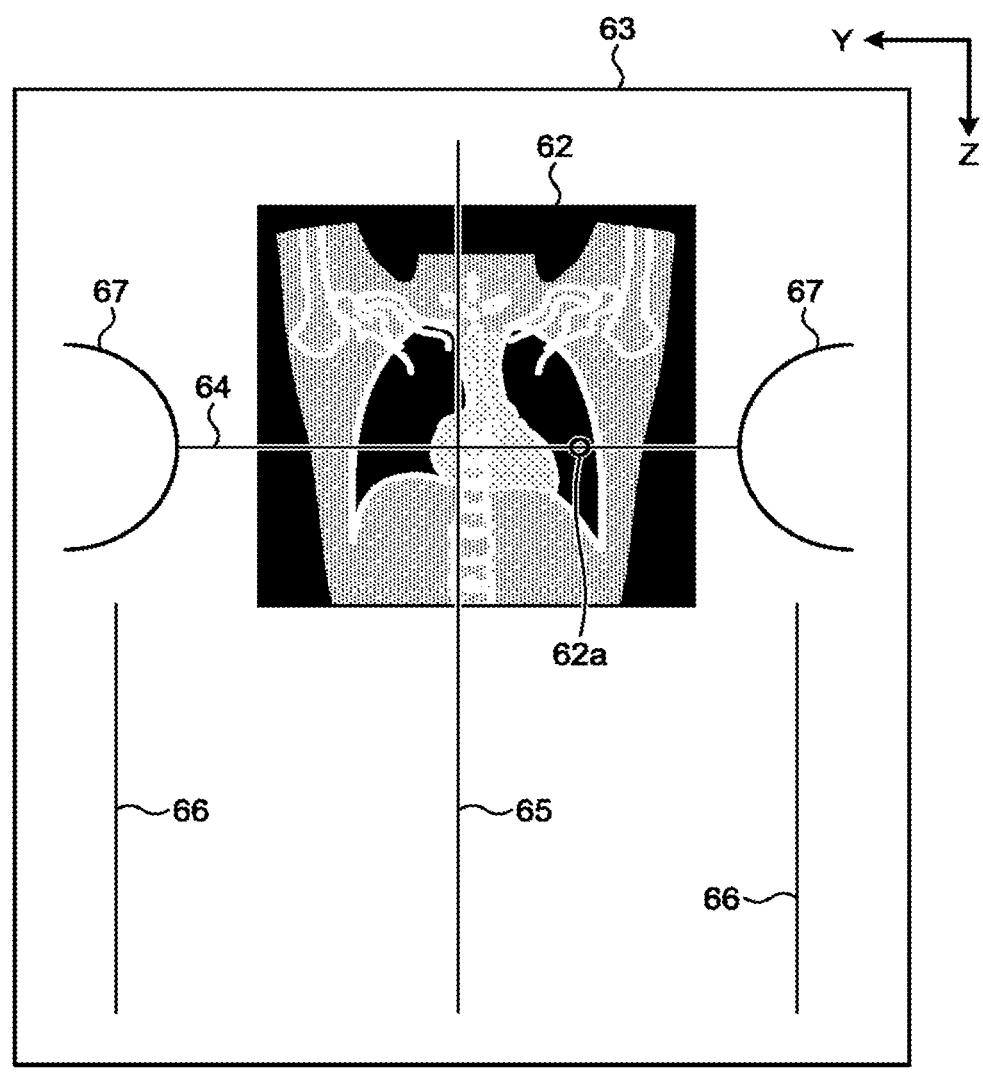
FIG. 9 is a drawing illustrating an example of a setting screen according to a second embodiment.
Figure 10:
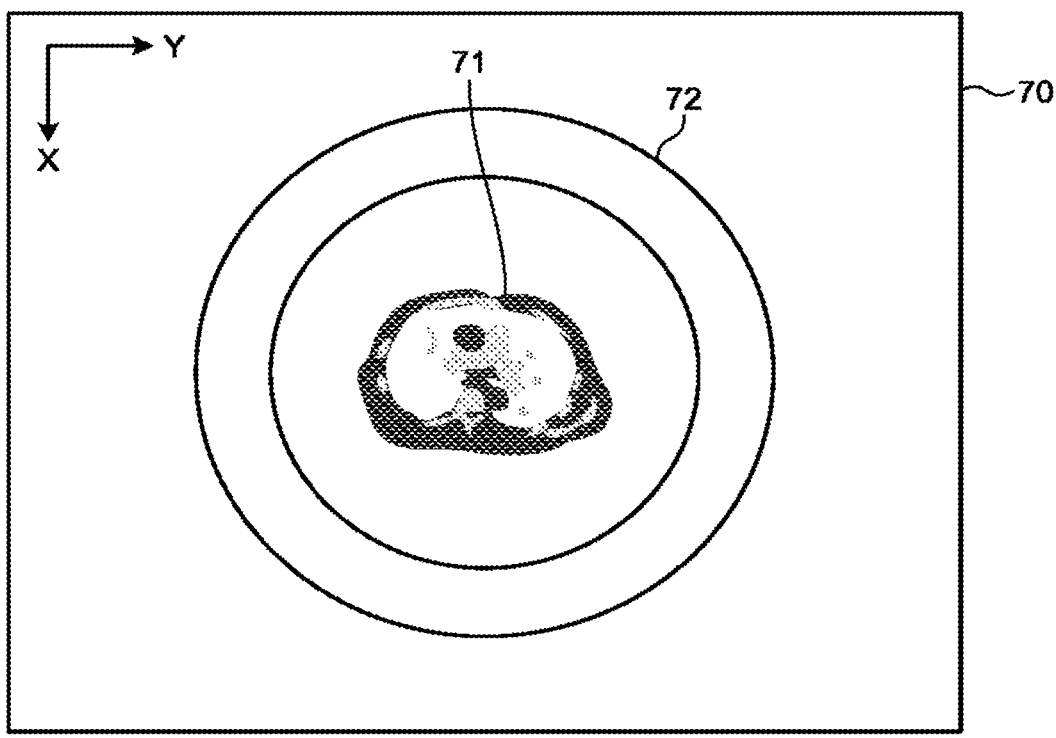
FIG. 10 is a drawing for explaining a method for setting an operation position on the setting screen according to the second embodiment.
Figure 11:
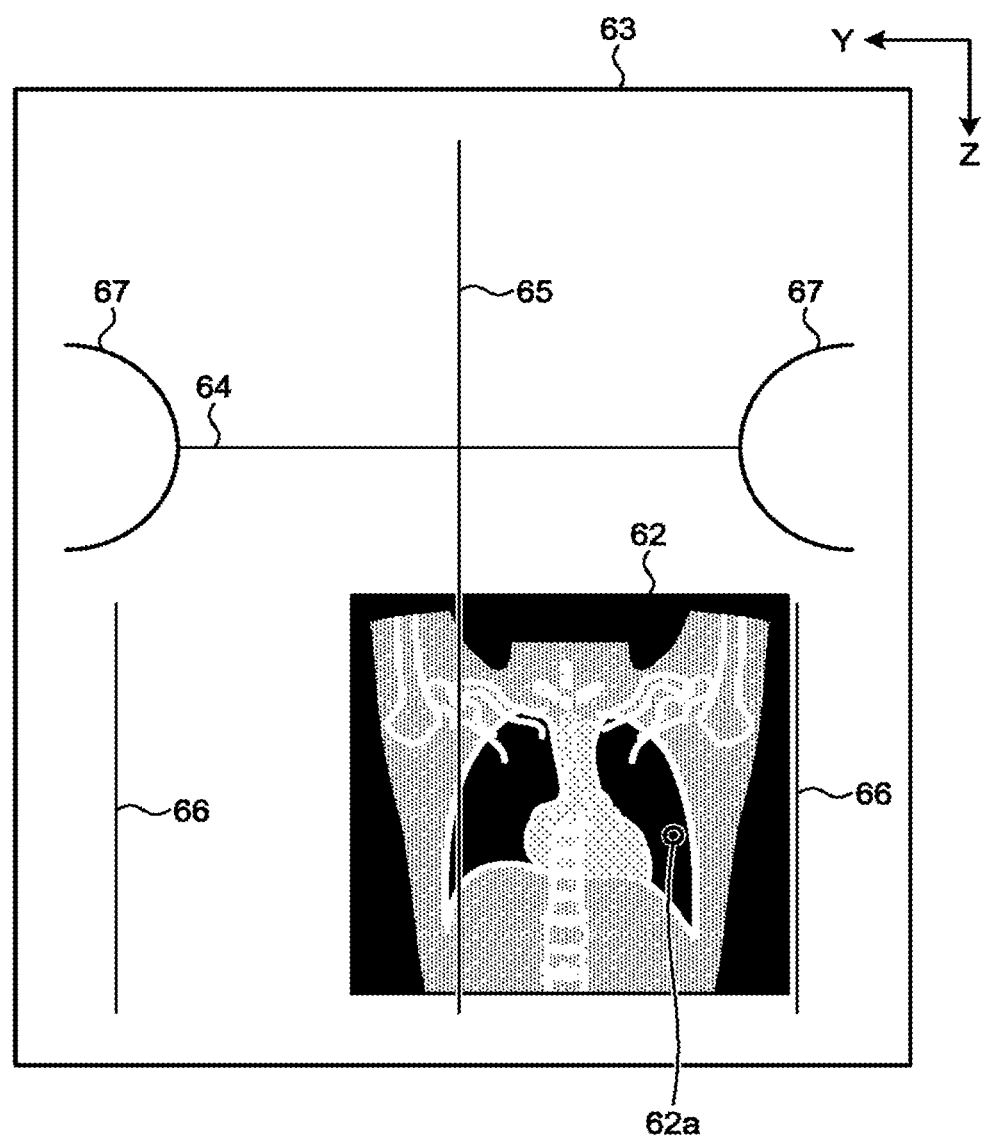
FIG. 11 is a drawing illustrating an example of a setting screen containing an axial image of the subject P.

Next, an embodiment in which an operation position is set by using a Graphical User Interface (GUI) will be explained as a second embodiment. FIGS. 9 to 11 are drawings illustrating examples of setting screens according to the second embodiment. The setting function 37a according to the second embodiment is configured to cause the display 32 to display a setting screen 63 illustrated in FIGS. 9 and 11 and a setting screen 70 illustrated in FIG. 10.

The setting screen 63 contains a coronal image 62 of the subject P. On the setting screen 63, the coronal image 62 is displayed so as to be movable by the practitioner. Further, the setting screen 63 contains a line 64 expressing the scan surface, a median line (the median line of the opening of the gantry 10) 65, and lines 66 expressing a moveable range in left and right direction of the couchtop 22. The lines 66 represent an example of a figure indicating the moveable range of the couchtop 22. Further, the setting screen 63 contains images 67 indicating the gantry 10 that has formed therein the opening serving as the image taking space. Further, the coronal image 62 contains a puncture target site 62a. As illustrated by the example in FIG. 9, by operating the input circuitry 31, the practitioner sets the position of the coronal image 62 in the Z-axis direction (the body axis direction) in such a manner that the puncture target site 62a is overlaid on the line 64 expressing the scan surface. Further, by operating the input circuitry 31, the practitioner sets the position of the coronal image 62 in the Y-axis direction in such a manner that the subject P rendered in the coronal image 62 is positioned within the moveable range of the couchtop indicated by the lines 66 and is not in contact with the gantry indicated by the images 67. In this situation, when a puncture needle is to be inserted perpendicularly, it is possible to arrange the workspace for performing the puncture process to have a wide area, by positioning the puncture target site 62a to be near the median line 65. For this reason, when the puncture needle is to be inserted perpendicularly, the practitioner sets the position of the coronal image 62 in the Y-axis direction in such a manner that the puncture target site 62a is positioned near the median line 65. When the coronal image 62 is moved in the Y-axis direction, an axial image 71 (explained later) also moves in the Y-axis direction in conjunction therewith.

FIG. 10 is a drawing illustrating an example of the setting screen containing an axial image of the subject P. The setting screen 70 illustrated in FIG. 10 contains an image 72 indicating the gantry and the axial image 71 of the subject P. The axial image 71 is displayed on the setting screen 70 so as to be movable by the practitioner. The axial image 71 contains an image taking site of the subject P. By operating the input circuitry 31, the practitioner sets the position of the axial image 71 in the X-axis direction in such a manner that the subject P rendered in the axial image 71 is not in contact with the gantry indicated by the image 72. On the setting screen 70, it is also possible to set the position of the axial image 71 in the Y-axis direction. In that situation, when the axial image 71 is moved in the Y-axis direction, the coronal image 62 also moves in the Y-axis direction in conjunction therewith. In this manner, the processing circuitry 37 causes the display 32 to display the median line 65 of the opening of the gantry 10 and the lines 66 indicating the moveable range of the couchtop 22, together with the coronal image 62 and the images 67. In this situation, the processing circuitry 37 may cause the display 32 to display at least one selected from between the median line 65 of the opening of the gantry 10 and the lines 66 indicating the moveable range of the couchtop 22, together with the coronal image 62 and the images 67. Further, the setting function 37a sets a target position in the real space, on the basis of a relative positional relationship, for example, among the images 67 and the image 72 rendering the gantry and the coronal image 62 and the axial image 71 rendering the subject P. The images 67 and the image 72 rendering the gantry are examples of the first image. Further, the coronal image 62 and the axial image 71 containing the image taking site are examples of the second image.

As explained above, the setting function 37a causes the display 32 to display the line 64, the median line 65, and the lines 66.

FIG. 11 is a drawing for explaining an example of a method for setting an operation position on the setting screen according to the second embodiment. As illustrated by the example in FIG. 11, by operating the input circuitry 31, the practitioner sets the position of the coronal image 62 in the Z-axis direction in such a manner that the puncture target site 62a is positioned at the front of the practitioner. As a result, the practitioner is able to easily operate the puncture needle. Further, by operating the input circuitry 31, the practitioner sets, as the position of the coronal image 62 in the Y-axis direction, such a position in the Y-axis direction that allows the subject P rendered in the coronal image 62 to be positioned within the moveable range of the couchtop indicated by the lines 66 and that makes it possible for the practitioner to easily apply a force (or to easily perform a sensitive operation). Further, on the setting screen 70 illustrated in FIG. 10 explained above, by operating the input circuitry 31, the practitioner sets the position of the axial image 71 in the X-axis direction in such a manner that the subject P rendered in the axial image 71 is not in contact with the gantry indicated by the image 72. Further, the setting function 37a sets an operation position in the real space, on the basis of a relative positional relationship among the images 67 and the image 72 rendering the gantry and the coronal image 62 and the axial image 71 rendering the subject P. In other words, the processing circuitry 37 sets the operation position of the couchtop 22, by using the configuration in which the second image containing the puncture target site of the subject P moves relative to the first image rendering the gantry 10, on the display screen of the display 32, in response to the operation. Further, the processing circuitry 37 estimates the position of the subject P in the real space on the basis of the position of the second image that has been moved and sets the estimated position as the operation position.

In this situation, on the setting screen 70 illustrated in the example in FIG. 11, when the subject P is not sufficiently pulled out in the Z-axis direction, it is suspected that the head of the subject P and the like may remain in the image taking space of the gantry indicated by the image 72. In that situation, when the axial image 71 is moved on the setting screen 70, there is a possibility that the head of the subject P remaining in the image taking space may come into contact with the gantry 10. When volume data of an entire body of the subject P has been obtained, the setting function 37a is able to judge whether or not the head of the subject or the like has a possibility of coming into contact with the gantry by using the volume data.

In this situation, in the second embodiment, when there is volume data of only a part of the subject P, for example, the setting function 37a is able to judge whether or not the head of the subject P or the like has a possibility of coming into contact with the gantry, even when the volume data of the head of the subject P has not been obtained. For example, the setting function 37a extracts an anatomical feature point (hereinafter, "anatomical landmark") from the volume data of the subject P. After that, the setting function 37a generates information that keeps an identification code used for identifying the extracted anatomical landmark in correspondence with the position (the coordinates) of the feature point. Subsequently, the setting function 37a estimates the site not included in the X-ray CT data of the subject P and complements the data, by using a model of a subject having a similar positional relationship for the anatomical landmark. After that, the setting function 37a judges whether or not the estimated site is to come into contact with the gantry.

Figures 12, 13:
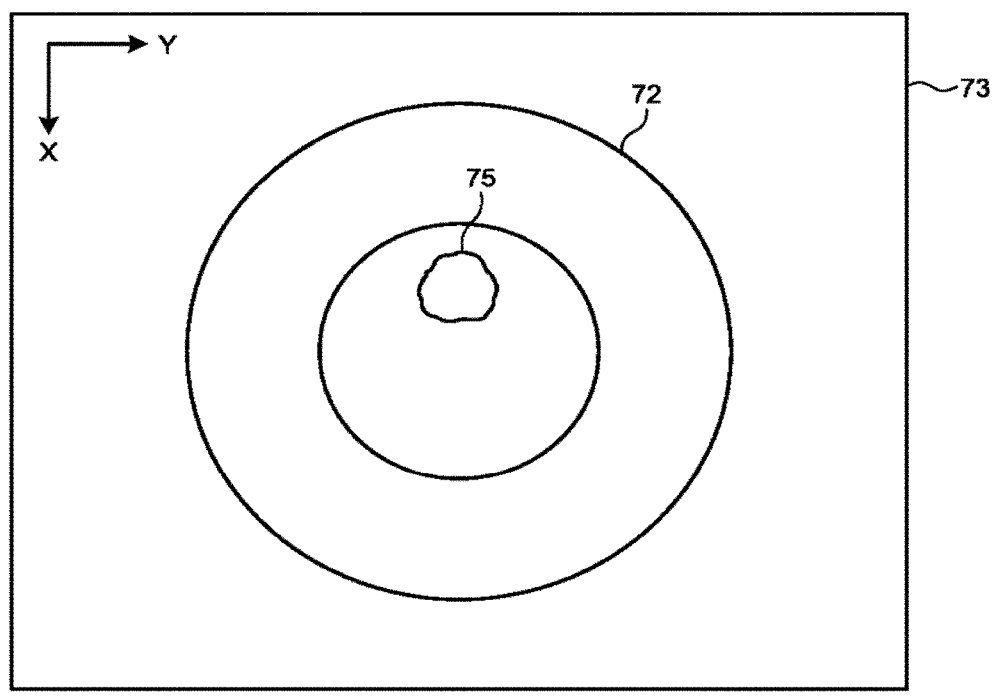
FIG. 12 is a drawing illustrating an example of a screen indicating a positional relationship between the head of the subject P that is estimated and the gantry.
FIG. 13 is a drawing illustrating an example of a data structure of a database according to a third embodiment.

Further, by causing the display 32 to display an image rendering the estimated site together with the image 72 rendering the gantry, the setting function 37a is capable of enabling the practitioner to understand the positional relationship between the estimated site and the gantry. The image rendering the estimated site is an example of the fifth image. FIG. 12 is a drawing illustrating an example of a screen indicating a positional relationship between the head of the subject P that was estimated and the gantry. As illustrated by the example in FIG. 12, the setting function 37a causes the display 32 to display a screen 73 containing an image 75 rendering an estimated head and the image 72 rendering the gantry. With this configuration, it is possible to enable the practitioner to understand the positional relationship between the head of the subject P and the gantry.

The example is explained above in which the target position and the operation position are set by using the coronal image 62 and the axial image 71; however, it is also acceptable to set a target position and an operation position by using two or more selected from among a coronal image of the subject P, an axial image of the subject P, and a sagittal image of the subject P. The target position and the operation position are examples of the predetermined position of the couchtop 22.

The second embodiment has thus been explained. According to the second embodiment, it is possible to move the subject P to the position where the practitioner is able to easily perform the puncture process, similarly to the first embodiment.

Third Embodiment

It is also possible to consider that the operation position is unique in correspondence with the physique and the dominant arm of the practitioner. For this reason, it is also possible to use a database storing therein operation positions so as to be kept in correspondence with information about physiques and dominant arms of practitioners and to derive an operation position suitable for the practitioner from the database. Thus, this embodiment will be explained as a third embodiment.

FIG. 13 is a drawing illustrating an example of a data structure of a database according to the third embodiment. As illustrated by the example in FIG. 13, a database 80 includes items such as "height", "weight", "dominant arm", "IN/OUT", "UP/DOWN", and "LEFT/RIGHT".

For example, the levels of body height registered under the item "height" are eleven levels from 140 cm to 190 cm increasing at increments of 5 cm. The levels of body weight registered under the item "weight" are fourteen levels from 35 kg to 100 kg increasing at increments of 5 kg. The types of dominant arms registered under the item "dominant arm" are two types, namely, the right arm and the left arm. In the present example, the total number of records in the database 80 is 308 (11×14×2). In other words, the database 80 has registered therein all the combinations made up of the levels of height, the levels of weight, and the types of dominant arms.

Registered under the item "IN/OUT" are the Z-axis values of operation positions where the practitioner is able to easily perform a puncture process, the values being statistically calculated with respect to all the combinations made up of the levels of height, the levels of weight, and the types of dominant arms. Registered under the item "UP/DOWN" are the X-axis values of operation positions where the practitioner is able to easily perform a puncture process, the values being statistically calculated with respect to all the combinations made up of the levels of height, the levels of weight, and the types of dominant arms. Registered under the item "LEFT/RIGHT" are the Y-axis values of operation positions where the practitioner is able to easily perform a puncture process, the values being statistically calculated with respect to all the combinations made up of the levels of height, the levels of weight, and the types of dominant arms. As explained herein, the database 80 has registered therein the operation positions where the practitioner is able to easily perform a puncture process, with respect to all the combinations made up of the levels of height, the levels of weight, and the types of dominant arms. In other words, the database 80 has stored therein the operation position corresponding to each of the plurality of pieces of physique information including the body weights and the body heights. More specifically, the database 80 has stored therein the pieces of information that are related to the plurality of operation positions (the puncture positions) of the couchtop 22 and that correspond to the pieces of unique information of a plurality of practitioners who each apply a manipulation to the subject P. The database 80 is stored in the storage circuitry 35.

Further, the setting function 37a according to the third embodiment is configured to receive physique information (the height and the weight) and information about the dominant arm of the practitioner from the practitioner. The physique information and the dominant arm information of the practitioner are examples of the unique information of the practitioner. For example, the setting function 37a causes the display 32 to display a receiving screen used for receiving an input of the physique information and the dominant arm information of the practitioner from the practitioner. In this manner, the setting function 37a obtains the physique information and the dominant arm information of the practitioner received on the receiving screen. The practitioner whose unique information has been received is the practitioner who applies a manipulation and represents an example of the first practitioner. Further, by using the physique information and the dominant arm information of the practitioner received on the receiving screen, the setting function 37a identifies a record to which the physique information and the dominant arm information of the practitioner are most similar, from among all the records in the database 80. After that, the setting function 37a obtains the operation position registered in the identified record.

After that, the couchtop controlling function 37b according to the third embodiment transmits an instruction to move the couchtop 22 to the operation position obtained by the setting function 37a, to the scan controlling circuitry 33. In other words, when a first practitioner is to apply a manipulation, the processing circuitry 37 controls the couch driving device 21 so as to move the couchtop 22 to the puncture position indicated by a piece of information related to the puncture position corresponding to the unique information pertaining to the first practitioner, the piece of information being among the pieces of information that are related to the plurality of operation positions and are stored in the storage circuitry 35. More specifically, the processing circuitry 37 obtains a first piece of unique information that is the unique information of the first practitioner and further controls, on the basis of the first piece of unique information, the couch driving device 21 so as to move the couchtop 22 to the puncture position indicated by a piece of information related to the puncture position corresponding to the first piece of unique information, the piece of information being among the pieces of information that are related to the plurality of puncture positions and are stored in the storage circuitry 35. Accordingly, the couchtop 22 is moved to the position suitable for the physique and the dominant arm of the practitioner. In other words, the couchtop controlling function 37b moves the couchtop 22 to the operation position corresponding to the physique information of the practitioner. Consequently, it is possible to move the subject to the position where the practitioner is able to easily perform the puncture process.

The third embodiment has thus been explained. According to the third embodiment, it is possible to move the subject P to the position where the practitioner is able to easily perform the puncture process, similarly to the first embodiment.

By using the X-ray CT apparatus according to at least one aspect of the embodiments described above, it is possible to move the subject P to the position where the practitioner is able to easily perform the puncture process.

While a number of embodiments of the present disclosure have been described, these embodiments are presented by way of examples only, and are not intended to limit the scope of the inventions. These exemplary embodiments may be carried out in a variety of other forms; furthermore, various omissions, substitutions, and changes may be made without departing from the spirit of the inventions. Those embodiments and the modifications are covered by the inventions defined in the accompanying claims and equivalents thereof, in the same manner as those embodiments and the modifications would fall within the scope and spirits of the inventions.

Fourth Embodiment

It is also possible to consider that the target position and the operation position are unique in correspondence with the physique of the subject P, in addition to the physique and the dominant arm of the practitioner. Thus, it is also acceptable to use a database (a first operation position database) storing therein operation positions so as to be kept in correspondence with pieces of information about the physiques of the subject P or the like (pieces of unique information of the subject P), in addition to the pieces of information about the physiques and the dominant arms of the practitioner (the pieces of unique information of the practitioner) and to derive an operation position suitable for the practitioner and the subject P from the first operation position database.

Further, it is also acceptable to use a database (a first target position database) storing therein target positions so as to be kept in correspondence with the unique information of the practitioner and the unique information of the subject P and to derive a target position suitable for the practitioner and the subject P from the first target position database.

Thus, this embodiment will be explained as a fourth embodiment.

FIG. 14 is a drawing illustrating an example of a data structure of the first operation position database according to the fourth embodiment. As illustrated by the example in FIG. 14, a first operation position database 81 includes items such as "height of practitioner", "weight of practitioner", "dominant arm of practitioner", "height of subject", "weight of subject", "IN/OUT", "UP/DOWN", and "LEFT/RIGHT". The first operation position database 81 is stored in the storage circuitry 35.

For example, the levels of body height of practitioners registered under the item "height of practitioner" are eleven levels from 140 cm to 190 cm increasing at increments of 5 cm. The levels of body weight of practitioners registered under the item "weight of practitioner" are fourteen levels from 35 kg to 100 kg increasing at increments of 5 kg. The types of dominant arms of practitioners registered under the item "dominant arm of practitioner" are two types, namely, the right arm and the left arm. The levels of body height of subjects P registered under the item "height of subject" are twenty-three levels from 80 cm to 190 cm increasing at increments of 5 cm. The levels of body weight of subjects P registered under the item "weight of subject" are seventeen levels from 20 kg to 100 kg increasing at increments of 5 kg. In the present example, the total number of records in the first operation position database 81 is 120,428 (11×14×2× 23×17). In other words, the first operation position database 81 has registered therein all the combinations made up of the levels of height of the practitioner, the levels of weight of the practitioner, the types of dominant arms of the practitioner, the levels of height of the subject P, and the levels of the weight of the subject P.

Registered under the item "IN/OUT" are the Z-axis values of operation positions that are either obtained from simulations or statistically calculated, with respect to all the combinations made up of the levels of height of the practitioner, the levels of weight of the practitioner, the types of dominant arms of the practitioner, the levels of height of the subject P, and the levels of weight of the subject P. In the present example in the fourth embodiment, the operation position denotes a position of the couchtop 22 where, for example, the practitioner is able to easily perform the puncture process while the subject P is not in contact with the gantry 10.

Registered under the item "UP/DOWN" are the X-axis values of operation positions that are either obtained from simulations or statistically calculated, with respect to all the combinations made up of the levels of height of the practitioner, the levels of weight of the practitioner, the types of dominant arms of the practitioner, the levels of height of the subject P, and the levels of weight of the subject P.

Registered under the item "LEFT/RIGHT" are the Y-axis values of operation positions that are either obtained from simulations or statistically calculated, with respect to all the combinations made up of the levels of height of the practitioner, the levels of weight of the practitioner, the types of dominant arms of the practitioner, the levels of height of the subject P, and the levels of weight of the subject P.

As explained above, the first operation position database 81 has registered therein the operation positions with respect to all the combinations made up of the levels of height of the practitioner, the levels of weight of the practitioner, the types of dominant arms of the practitioner, the levels of height of the subject P, and the levels of weight of the subject P. In other words, the first operation position database 81 has stored therein the operation position corresponding to each of the plurality of combinations made up of the pieces of unique information of the practitioner and the pieces of unique information of the subject P. In this manner, the first operation position database 81 stored in the storage circuitry 35 has stored therein the pieces of information related to the plurality of puncture positions corresponding to the plurality of combinations made up of the pieces of unique information of the plurality of practitioners and the pieces of unique information of the plurality of subjects P.

FIG. 15 is a drawing illustrating an example of a data structure of the first target position database according to the fourth embodiment. As illustrated by the example in FIG. 15, a first target position database 82 includes items such as "height of practitioner", "weight of practitioner", "dominant arm of practitioner", "height of subject", "weight of subject", "IN/OUT", "UP/DOWN", and "LEFT/RIGHT". The first target position database 82 is stored in the storage circuitry 35.

The contents registered under the items "height of practitioner", "weight of practitioner", "dominant arm of practitioner", "height of subject", and "weight of subject" in the first target position database 82 are the same as the contents registered under the items "height of practitioner", "weight of practitioner", "dominant arm of practitioner", "height of subject", and "weight of subject" in the first operation position database 81 illustrated in FIG. 14. Thus, the explanation thereof will be omitted. In other words, the total number of records in the first target position database 82 is equal to the total number of records (120,428) in the first operation position database 81 explained above. In this manner, the first target position database 82 has registered therein all the combinations made up of the levels of height of the practitioner, the levels of weight of the practitioner, the types of dominant arms of the practitioner, the levels of height of the subject P, and the levels of weight of the subject P.

Registered under the item "IN/OUT" are the Z-axis values of target positions that are either obtained from simulations or statistically calculated, with respect to all the combinations made up of the levels of height of the practitioner, the levels of weight of the practitioner, the types of dominant arms of the practitioner, the levels of height of the subject P, and the levels of weight of the subject P. In the present example in the fourth embodiment, the target position denotes a position of the couchtop 22 where, for example, it is possible to image the puncture target site and the puncture needle rendered in the X-ray CT image while the subject P is not in contact with the gantry 10.

Registered under the item "UP/DOWN" are the X-axis values of target positions that are either obtained from simulations or statistically calculated, with respect to all the combinations made up of the levels of height of the practitioner, the levels of weight of the practitioner, the types of dominant arms of the practitioner, the levels of height of the subject P, and the levels of weight of the subject P.

Registered under the item "LEFT/RIGHT" are the Y-axis values of target positions that are either obtained from simulations or statistically calculated, with respect to all the combinations made up of the levels of height of the practitioner, the levels of weight of the practitioner, the types of dominant arms of the practitioner, the levels of height of the subject P, and the levels of weight of the subject P.

As explained above, the first target position database 82 has registered therein the target positions with respect to all the combinations made up of the levels of height of the practitioner, the levels of weight of the practitioner, the types of dominant arms of the practitioner, the levels of height of the subject P, and the levels of weight of the subject P. In other words, the first target position database 82 has stored therein the target position corresponding to each of the plurality of combinations made up of the pieces of unique information of the practitioner and the pieces of unique information of the subject P. In this manner, the storage circuitry 35 has stored therein the pieces of information related to the plurality of target positions (image taking positions) corresponding to the plurality of combinations made up of the pieces of unique information of the plurality of practitioners and the pieces of unique information of the plurality of subjects.

Further, the setting function 37a according to the fourth embodiment is configured to receive the unique information of the practitioner (the information related to the height, the weight, and the dominant arm of the practitioner) and the unique information of the subject P (the height and the weight of the subject P), from the practitioner. For example, the setting function 37a causes the display 32 to display a receiving screen used for receiving an input of the unique information of the practitioner and the unique information of the subject P, from the practitioner.

After that, when the "move to operation position" button 54 is pressed by the practitioner, the setting function 37a identifies, by using the unique information of the practitioner and the unique information of the subject P received on the receiving screen, a record registering therein unique information of a practitioner and unique information of a subject P to which the unique information of the practitioner and the unique information of the subject P received on the receiving screen are most similar, from among all the records in the first operation position database 81. After that, the setting function 37a obtains the operation position registered in the identified record.

After that, the couchtop controlling function 37b according to the fourth embodiment transmits an instruction to move the couchtop 22 to the operation position obtained by the setting function 37a, to the scan controlling circuitry 33. In other words, the processing circuitry 37 controls the couch driving device 21 so as to move the couchtop 22 to the puncture position indicated by a piece of information related to a puncture position corresponding to the unique information of the first practitioner and the unique information of a first subject to whom a manipulation is applied by the first practitioner, the piece of information being among the pieces of information that are related to the plurality of puncture positions and are stored in the storage circuitry 35. Accordingly, the couchtop 22 is moved to the operation position suitable for the physique and the dominant arm of the practitioner and the physique of the subject P. In other words, the couchtop controlling function 37b moves the couchtop 22 to the operation position corresponding to the unique information of the practitioner and the unique information of the subject P. Consequently, it is possible to move the subject P to the position where the practitioner is able to easily perform the puncture process while the subject P is not in contact with the gantry 10.

Further, when the "move to target position" button 44 is pressed by the practitioner, the setting function 37a according to the fourth embodiment identifies, by using the unique information of the practitioner and the unique information of the subject P received on the receiving screen, a record registering therein unique information of a practitioner and unique information of a subject P to which the unique information of the practitioner and the unique information of the subject P received on the receiving screen are most similar, from among all the records in the first target position database 82. After that, the setting function 37a obtains the target position registered in the identified record.

After that, the couchtop controlling function 37b according to the fourth embodiment transmits an instruction to move the couchtop 22 to the target position obtained by the setting function 37a, to the scan controlling circuitry 33. In other words, the processing circuitry 37 controls the couch driving device 21 so as to move the couchtop 22 to the image taking position indicated by a piece of information related to the image taking position corresponding to the unique information of the first practitioner and the unique information of the first subject that is the subject to whom a manipulation is applied by the first practitioner, the piece of information being among the pieces of information that are related to the plurality of image taking positions and are stored in the storage circuitry 35. Accordingly, the couchtop 22 is moved to the target position suitable for the physique and the dominant arm of the practitioner and the physique of the subject P. In other words, the couchtop controlling function 37b moves the couchtop 22 to the target position corresponding to the unique information of the practitioner and the unique information of the subject P. Consequently, it is possible to move the subject P to the position where it is possible to image the puncture target site and the puncture needle rendered in the X-ray CT image, while the subject P is not in contact with the gantry 10.

The fourth embodiment has thus been explained. According to the fourth embodiment, it is possible to move the subject P to the position where the practitioner is able to easily perform the puncture process, similarly to the first embodiment.

In the fourth embodiment, the first operation position database 81 and the first target position database 82 may be integrated into a single database, and the single database may be used to execute the above-described various processes. For example, a single database registered in association with the levels of body height of practitioners, the levels of body weight of practitioners, the types of dominant arms of practitioners, the levels of body height of subjects P, the levels of body weight of subjects P, the Z-axis values, the X-axis values and the Y-axis values of operation positions that are either obtained from simulations or statistically calculated, and the Z-axis values, the X-axis values and the Y-axis values of target positions that are either obtained from simulations or statistically calculated may be used to execute the above-described various processes.

Fifth Embodiment

It is also possible to consider that the target position and the operation position are unique in correspondence with at least one selected from between the target region and the manipulation (the puncture process), in addition to the physique and the dominant arm of the practitioner. FIGS. 16 to 21 are drawings for explaining that the target position is unique in correspondence with at least one selected from between the target region and the manipulation.

Figure 16:
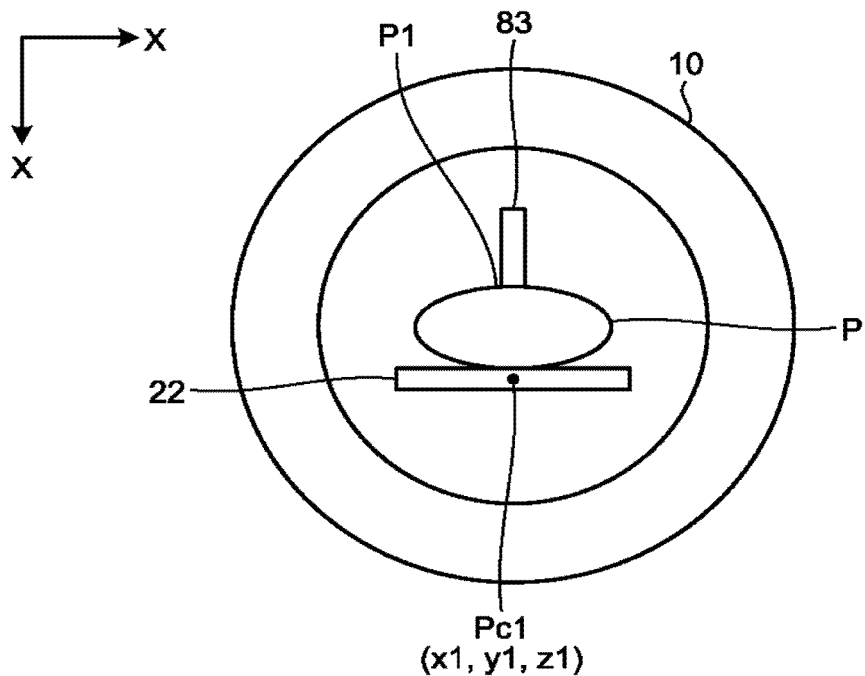
FIG. 16 is a drawing for explaining that a target position is unique in correspondence with at least one selected from between a target region and a manipulation.

For example, FIG. 16 is a drawing illustrating an example of a target position in a situation where the target region is a front part P1 selected from the entire abdomen of the subject P, while the manipulation is a biopsy. As illustrated in FIG. 16, when the target region is the front part P1, the posture of the subject P is a supine position. Further, when the manipulation is a biopsy, the length of a puncture needle 83 used for the biopsy is relatively short and may be, for example, approximately 20 cm. In the present example, to obtain an X-ray CT image rendering the target region and the puncture needle, it is a common practice to position the target region at the center of an image taking space at the time of an image taking process. In the example illustrated in FIG. 16, because the puncture needle 83 is relatively short, it is possible to arrange the front part P1 serving as the target region to be positioned at the center of the image taking space, without the puncture needle 83 being in contact with the gantry 10. The target position of the couchtop 22 in that situation is Pc1 (x1,y1,z1), as indicated in FIG. 16.

Figure 17:
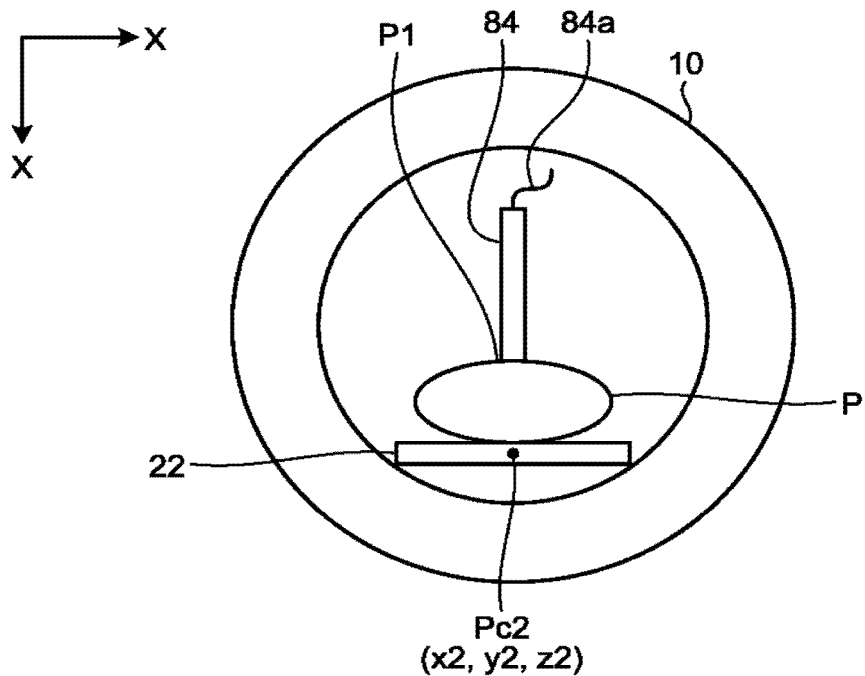
FIG. 17 is another drawing for explaining that a target position is unique in correspondence with at least one selected from between a target region and a manipulation.

Further, for example, FIG. 17 is a drawing illustrating an example of the target position in a situation where the target region is the front part P1 selected from the entire abdomen of the subject P, while the manipulation is a radiofrequency ablation (RFA). As illustrated in FIG. 17, when the target region is the front part P1, the posture of the subject P is a supine position, similarly to the example in FIG. 16. Further, when the manipulation is an RFA, the length of a puncture needle 84 used for the RFA is longer than the puncture needle 83 used for biopsies and may be, for example, approximately 30 cm. Further, the puncture needle 84 used for the RFA is provided with a cable 84*a* configured to relay radio waves to the puncture needle 84. The length totaling the cable 84*a* and the puncture needle 84 is longer than the length of the puncture needle 83. Thus, if an attempt was made to arrange the front part P1 serving as the target region to be positioned at the center of the image taking space, the puncture needle 84 and the cable 84*a* would come into contact with the gantry 10. For this reason, in terms of the X-axis direction (the up-and-down direction), a target position Pc2 (x2,y2,z2) is in a position advanced in the positive direction on the X-axis from the target position Pc1 (x1,y1,z1) illustrated in FIG. 16 (i.e., Pc2 is lower than Pc1 (x1,y1,z1)).

In this situation, when FIG. 16 is compared with FIG. 17, it is observed that the target positions are different from each other, because the manipulations are mutually different, although the postures of the subject P are the same as each other. In other words, the target positions are different because the types of the employed devices (the puncture needles in the present example) are different in accordance with the manipulations. In other words, the target positions are different in accordance with either the manipulations or the devices employed for the manipulations.

Figure 18:
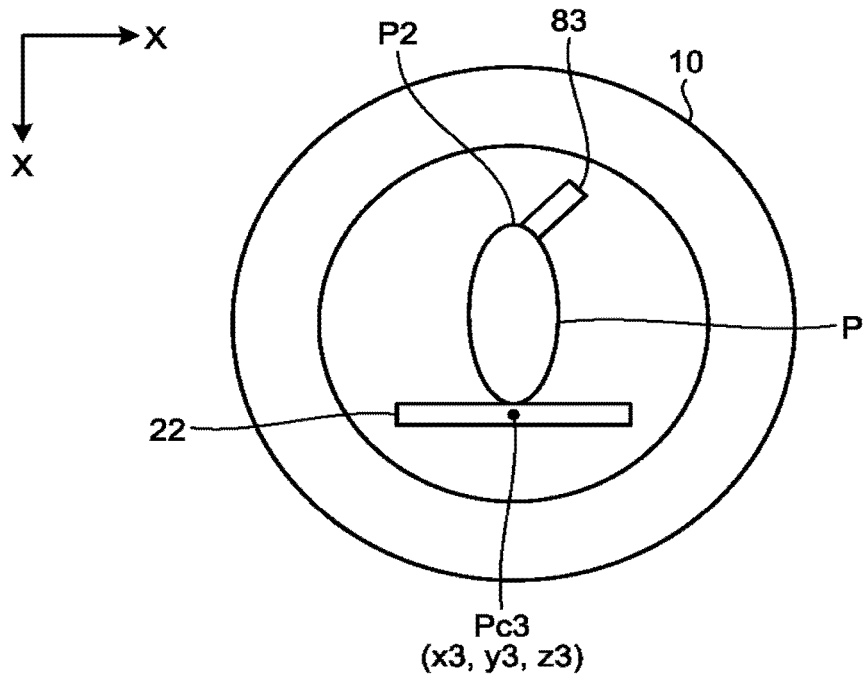
FIG. 18 is yet another drawing for explaining that a target position is unique in correspondence with at least one selected from between a target region and a manipulation.

For example, FIG. 18 is a drawing illustrating an example of the target position in a situation where the target region is a back-side part P2 selected from the entire abdomen of the subject P, while the manipulation is a biopsy. As illustrated in FIG. 18, when the target region is the back-side part P2 selected from the entire abdomen, the posture of the subject P is lying down on his/her side. Further, when the manipulation is a biopsy, the puncture needle 83 is used, similarly to the example in FIG. 16. In the example in FIG. 18, because the posture of the subject P is lying down on his/her side, the width of the subject P in the X-axis direction (the up-and-down direction) within the image taking space is relatively large. Thus, if an attempt was made to arrange the part P2 serving as the target region to be positioned at the center of the image taking space, the couchtop 22 would come into contact with the gantry 10. For this reason, in terms of the X-axis direction (the up-and-down direction), a target position Pc3 (x3,y3,z3) illustrated in the example in FIG. 18 is in a position advanced in the positive direction on the X-axis from the target position Pc1 (x1,y1,z1) illustrated in FIG. 16.

In this situation, when FIG. 16 is compared with FIG. 18, it is observed that the target positions are different from each other, because the postures of the subject P are mutually different, although the manipulations are the same as each other. In this situation, the posture of the subject P varies in accordance with the target region. In other words, the target positions are different in accordance with either the postures of the subject P or the target regions.

Figure 19:
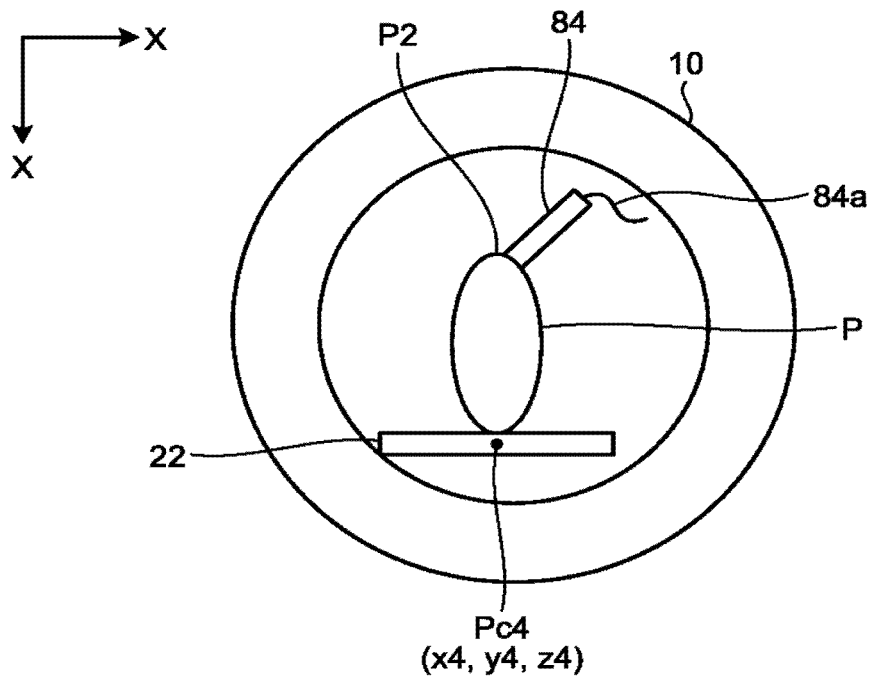
FIG. 19 is yet another drawing for explaining that a target position is unique in correspondence with at least one selected from between a target region and a manipulation.

Further, for example, FIG. 19 is a drawing illustrating an example of the target position in a situation where the target region is the back-side part P2 selected from the entire abdomen of the subject P, while the manipulation is an RFA. As illustrated in FIG. 19, when the target region is the back-side part P2 selected from the entire abdomen, the posture of the subject P is lying on his/her side, similarly to the example in FIG. 18. Further, when the manipulation is an RFA, the puncture needle 84 is used, similarly to the example illustrated in FIG. 17. Further, in the example in FIG. 19, because the posture of the subject P is lying on his/her side, the width of the subject P in the X-axis direction (the up-and-down direction) within the image taking space is relatively large, similarly to the example in FIG. 18. Thus, if an attempt was made to arrange the part P2 serving as the target region to be positioned at the center of the image taking space, the couchtop 22 would come into contact with the gantry 10. For this reason, in terms of the X-axis direction (the up-and-down direction), a target position Pc4 (x4,y4,z4) in the example in FIG. 19 is in a position advanced in the positive direction on the X-axis from the target position Pc2 (x2,y2,z2) illustrated in FIG. 17. Further, for example, in terms of the Y-axis direction (the left-and-right direction), the target position Pc4 (x4,y4,z4) is positioned on the positive direction side on the Y-axis, relative to the target position Pc2 (x2,y2,z2) illustrated in FIG. 17.

When FIG. 17 is compared with FIG. 19, it is observed that the target positions are different from each other, because the postures of the subject P are mutually different, although the manipulations are the same as each other. In this situation, as explained above, the posture of the subject P varies in accordance with the target region. In other words, the target positions are different in accordance with either the target regions or the postures of the subject P.

Figure 20:
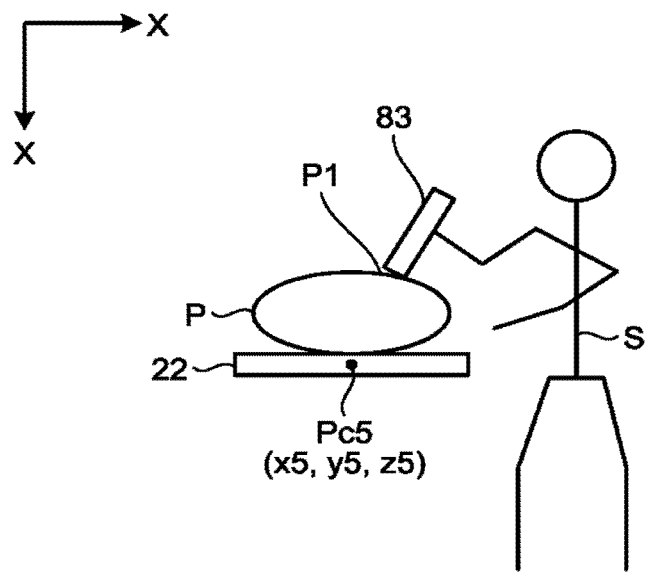
FIG. 20 is yet another drawing for explaining that a target position is unique in correspondence with at least one selected from between a target region and a manipulation.

Further, for example, FIG. 20 is a drawing illustrating an example of the operation position in a situation where the target region is the front part P1 selected from the entire abdomen of the subject P, while the manipulation is a biopsy. FIG. 20 illustrates the situation in which the practitioner S performs a biopsy by using the puncture needle 83. The operation position of the couchtop 22 in this situation is Pc5 (x5,y5,z5), as illustrated in FIG. 20.

Figure 21:
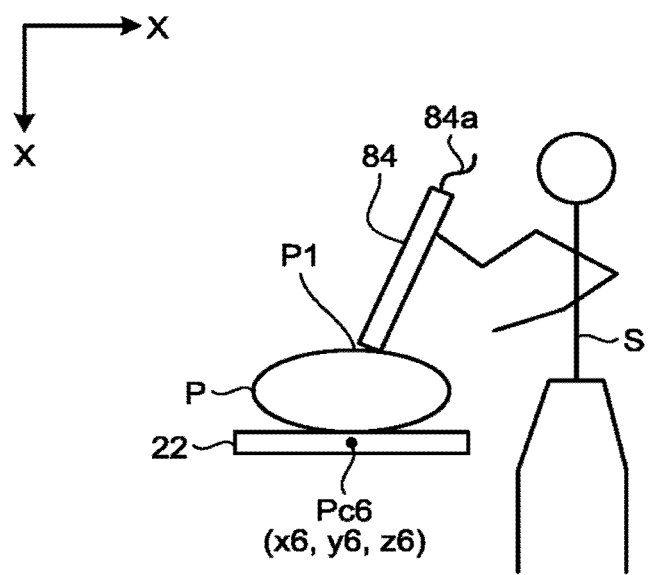
FIG. 21 is yet another drawing for explaining that a target position is unique in correspondence with at least one selected from between a target region and a manipulation.

Further, for example, FIG. 21 is a drawing illustrating an example of the operation position in a situation where the target region is the front part P1 selected from the entire abdomen of the subject P, while the manipulation is an RFA. FIG. 21 illustrates the situation in which the practitioner S performs the RFA by using the puncture needle 84. The operation position of the couchtop 22 in this situation is Pc6 (x6,y6,z6), as illustrated in FIG. 21.

In these situations, for example, because the puncture needle 83 is shorter than the puncture needle 84, the distance between the subject P and the hand location of the practitioner S is shorter when the biopsy is performed than when the RFA is performed. For this reason, in terms of the X-axis direction (the up-and-down direction), Pc5 (x5,y5,z5) is positioned on the negative direction side on the X-axis, relative to Pc6 (x6,y6,z6).

As FIG. 20 is compared with FIG. 21, it is observed that the operation positions are different from each other because the manipulations are mutually different, although the postures of the subject P are the same as each other. In other words, the operation positions are different in accordance with either the manipulations or the devices employed for the manipulations.

Further, because the widths of the subject P in the X-axis direction (the up-and-down direction) are different in accordance with the postures of the subject P, the operation positions are different from each other in accordance with either the target regions or the postures of the subject P.

As explained above, it is also considered that the target position and the operation position are unique in accordance with at least one selected from between the target region and the manipulation (the puncture process), in addition to the physique and the dominant arm of the practitioner, or the like.

Accordingly, it is also acceptable to use a database (a second operation position database) storing therein operation positions so as to be kept in correspondence with at least one selected from between target regions (or postures of the subject P) and manipulations (or devices employed for the manipulations) in addition to the pieces of information about the physiques and the dominant arms of the practitioner (the pieces of unique information of the practitioner) and to derive an operation position suitable for the unique information of the practitioner and at least one selected from between the target region (or the posture of the subject P) and the manipulation (or the device employed for the manipulation), from the second operation position database.

Further, it is also acceptable to use a database (a second target position database) storing therein target positions so as to be kept in correspondence with at least one selected from between target regions (or postures of the subject P) and manipulations (or devices employed for the manipulations) in addition to the pieces of information about the physiques and the dominant arms of the practitioner (the pieces of unique information of the practitioner) and to derive a target position suitable for the unique information of the practitioner and at least one selected from between the target region (or the posture of the subject P) and the manipulation (or the device employed for the manipulation), from the second target position database.

Thus, this embodiment will be explained as a fifth embodiment.

The following example describes the second operation position database storing therein the operation positions so as to be kept in correspondence with the target regions and the manipulations, in addition to the pieces of unique information of the practitioner. Further, the following also describes the second target position database storing therein the target positions so as to be kept in correspondence with the target regions and the manipulations in addition to the pieces of unique information of the practitioner.

FIG. 22 is a drawing illustrating an example of a data structure of the second operation position database according to the fifth embodiment. As illustrated by the example in FIG. 22, a second operation position database 85 includes items such as "height of practitioner", "weight of practitioner", "dominant arm of practitioner", "target region", "manipulation", "IN/OUT", "UP/DOWN", and "LEFT/RIGHT". The second operation position database 85 is stored in the storage circuitry 35.

The contents registered under the items "height of practitioner", "weight of practitioner", and "dominant arm of practitioner" in the second operation position database 85 are the same as the contents registered under the items "height of practitioner", "weight of practitioner", and "dominant arm of practitioner" in the first operation position database 81 illustrated in FIG. 14. Thus, the explanation thereof will be omitted.

The number of types of target regions registered under the item "target region" in the second operation position database 85 is n (where n is a natural number). The number of types of manipulations registered under the item "manipulation" is m (where m is a natural number). In the present example, the total number of records in the second operation position database 85 is 308×n×m (11×14×2×n×m). In other words, the second operation position database 85 has registered therein all the combinations made up of the levels of height of the practitioner, the levels of weight of the practitioner, the types of dominant arms of the practitioner, the types of target regions, and the types of manipulations.

Registered under the item "IN/OUT" are the Z-axis values of operation positions that are either obtained from simulations or statistically calculated, with respect to all the combinations made up of the levels of height of the practitioner, the levels of weight of the practitioner, the types of dominant arms of the practitioner, the types of target regions, and the types of manipulations. In the fifth embodiment, the operation position denotes a position of the couchtop 22 where, for example, the practitioner is able to easily perform the puncture process while the subject P is not in contact with the gantry 10.

Registered under the item "UP/DOWN" are the X-axis values of operation positions that are either obtained from simulations or statistically calculated, with respect to all the combinations made up of the levels of height of the practitioner, the levels of weight of the practitioner, the types of dominant arms of the practitioner, the types of target regions, and the types of manipulations.

Registered under the item "LEFT/RIGHT" are the Y-axis values of operation positions that are either obtained from simulations or statistically calculated, with respect to all the combinations made up of the levels of height of the practitioner, the levels of weight of the practitioner, the types of dominant arms of the practitioner, the types of target regions, and the types of manipulations.

As explained above, the second operation position database 85 has registered therein the operation positions where the practitioner is able to easily perform the puncture process while the subject P is not in contact with the gantry 10, with respect to all the combinations made up of the levels of height of the practitioner, the levels of weight of the practitioner, the types of dominant arms of the practitioner, the types of target regions, and the types of manipulations. In other words, the second operation position database 85 has stored therein the operation position corresponding to each of the plurality of combinations made up of the pieces of unique information of the practitioner, the types of target regions, and the types of manipulations. Accordingly, the storage circuitry 35 has stored therein the pieces of information related to the plurality of puncture positions corresponding to the plurality of combinations made up of the pieces of unique information of the plurality of practitioners, the target regions of the subject, and the manipulations applied to the subject.

FIG. 23 is a drawing illustrating an example of a data structure of the second target position database according to the fifth embodiment. As illustrated by the example in FIG. 23, a second target position database 86 includes items such as "height of practitioner", "weight of practitioner", "dominant arm of practitioner", "target region", "manipulation", "IN/OUT", "UP/DOWN", and "LEFT/RIGHT". The second target position database 86 is stored in the storage circuitry 35.

The contents registered under the items "height of practitioner", "weight of practitioner", "dominant arm of practitioner", "target region", and "manipulation" in the second target position database 86 are the same as the contents registered under the items "height of practitioner", "weight of practitioner", "dominant arm of practitioner", "target region", and "manipulation" in the second operation position database 85 illustrated in FIG. 22. Thus, the explanation thereof will be omitted. In other words, the total number of records in the second target position database 86 is equal to the total number of records (308×n×m) of the second operation position database 85 explained above. In this manner, the second target position database 86 has registered therein all the combinations made up of the levels of height of the practitioner, the levels of weight of the practitioner, the types of dominant arms of the practitioner, the types of target regions, and the types of manipulations.

Registered under the item "IN/OUT" are the Z-axis values of target positions that are either obtained from simulations or statistically calculated, with respect to all the combinations made up of the levels of height of the practitioner, the levels of weight of the practitioner, the types of dominant arms of the practitioner, the types of target regions, and the types of manipulations. In the present example in the fifth embodiment, the target position denotes a position of the couchtop 22 where, for example, it is possible to image the puncture target site and the puncture needle rendered in the X-ray CT image while the subject P is not in contact with the gantry 10.

Registered under the item "UP/DOWN" are the X-axis values of target positions that are either obtained from simulations or statistically calculated, with respect to all the combinations made up of the levels of height of the practitioner, the levels of weight of the practitioner, the types of dominant arms of the practitioner, the types of target regions, and the types of manipulations.

Registered under the item "LEFT/RIGHT" are the Y-axis values of target positions that are either obtained from simulations or statistically calculated, with respect to all the combinations made up of the levels of height of the practitioner, the levels of weight of the practitioner, the types of dominant arms of the practitioner, the types of target regions, and the types of manipulations.

As explained above, the second target position database 86 has registered therein the target positions where it is possible to image the puncture target site and the puncture needle rendered in the X-ray CT image while the subject P is not in contact with the gantry 10, with respect to all the combinations made up of the levels of height of the practitioner, the levels of weight of the practitioner, the types of dominant arms of the practitioner, the types of target regions, and the types of manipulations. In other words, the second target position database 86 has stored therein the target position corresponding to each of the plurality of combinations made up of the pieces of unique information of the practitioner, the types of target regions, and the types of manipulations. Accordingly, the storage circuitry 35 has stored therein the pieces of information related to the plurality of image taking positions corresponding to the plurality of combinations made up of the pieces of unique information of the plurality of practitioners, the target regions of the subject, and the manipulations applied to the subject.

Further, the setting function 37a according to the fifth embodiment receives the unique information of the practitioner (the information related to the height, the weight, and the dominant arm of the practitioner), the type of the target region, and the type of the manipulation, from the practitioner. For example, the setting function 37a causes the display 32 to display a receiving screen used for receiving an input of the unique information of the practitioner, the type of the target region, and the type of the manipulation, from the practitioner.

After that, when the "move to operation position" button 54 is pressed by the practitioner, the setting function 37a identifies, by using the unique information of the practitioner, the type of the target region, and the type of the manipulation received on the receiving screen, a record registering therein unique information of a practitioner, a type of a target region, and a type of a manipulation to which the unique information of the practitioner, the type of the target region, and the type of the manipulation received on the receiving screen are most similar, from among all the records in the second operation position database 85. After that, the setting function 37a obtains the operation position registered in the identified record.

After that, the couchtop controlling function 37b according to the fifth embodiment transmits an instruction to move the couchtop 22 to the operation position obtained by the setting function 37a, to the scan controlling circuitry 33. In other words, the processing circuitry 37 controls the couch driving device 21 so as to move the couchtop 22 to the image taking position indicated by a piece of information related to the image taking position corresponding to the unique information of the first practitioner and the unique information of the first subject to whom a manipulation is applied by the first practitioner, the piece of information being among the pieces of information that are related to the plurality of image taking positions and are stored in the storage circuitry 35. Accordingly, the couchtop 22 is moved to the operation position suitable for the physique and the dominant arm of the practitioner, the type of the target region, and the type of the manipulation. In other words, the couchtop controlling function 37b moves the couchtop 22 to the operation position corresponding to the unique information of the practitioner, the type of the target region, and the type of the manipulation. Consequently, it is possible to move the subject P to the position where the practitioner is able to easily perform the puncture process, while the subject P is not in contact with the gantry 10.

Further, when the "move to target position" button 44 is pressed by the practitioner, the setting function 37a according to the fifth embodiment identifies, by using the unique information of the practitioner, the type of the target region, and the type of the manipulation received on the receiving screen, a record registering therein unique information of a practitioner, a type of a target region, and a type of a manipulation to which the unique information of the practitioner, the type of the target region, and the type of the manipulation received on the receiving screen are most similar, from among all the records in the second target position database 86. After that, the setting function 37a obtains the target position registered in the identified record.

After that, the couchtop controlling function 37b according to the fifth embodiment transmits an instruction to move the couchtop 22 to the target position obtained by the setting function 37a, to the scan controlling circuitry 33. In other words, the processing circuitry 37 controls the couch driving device 21 so as to move the couchtop 22 to the image taking position indicated by a piece of information related to the image taking position corresponding to the unique information of the first practitioner, a first target region that is the target region of the first subject to whom a first manipulation is applied by the first practitioner, and the first manipulation, the piece of information being among the pieces of information that are related to the plurality of image taking positions and are stored in the storage circuitry 35. Accordingly, the couchtop 22 is moved to the target position suitable for the physique and the dominant arm of the practitioner, the type of the target region, and the type of the manipulation. In other words, the couchtop controlling function 37b moves the couchtop 22 to the target position corresponding to the unique information of the practitioner, the type of the target region, and the type of the manipulation. Consequently, it is possible to move the subject P to the position where it is possible to image the puncture target site and the puncture needle rendered in the X-ray CT image, while the subject P is not in contact with the gantry 10.

The fifth embodiment has thus been explained. According to the fifth embodiment, it is possible to move the subject P to the position where the practitioner is able to easily perform the puncture process, similarly to the first embodiment.

In the fifth embodiment, the second operation position database 85 and the second target position database 86 may each have an item "posture of subject" in place of the item "target region" and may each have registered therein types of postures of the subject P under the item "posture of subject".

Further, the setting function 37a according to the fifth embodiment may receive the type of the posture in place of the type of the target region, so as to obtain an operation position from the second operation position database 85 by using the received type of the posture, while implementing the same method as the method described above by which the operation position is obtained from the second operation position database 85 by using the type of the target region. Further, the setting function 37a may obtain a target position from the second target position database 86 by using the received type of the posture, while implementing the same method as the method described above by which the target position is obtained from the second target position database 86 by using the type of the target region.

Also, in the fifth embodiment, the second operation position database 85 and the second target position database 86 may each have an item "device" in place of the item "manipulation" and may each have registered therein types of devices employed for the manipulations under the item "device".

Further, the setting function 37a according to the fifth embodiment may receive the type of the device in place of the type of the manipulation, so as to obtain an operation position from the second operation position database 85 by using the received type of the device, while implementing the same method as the method described above by which the operation position is obtained from the second operation position database 85 by using the type of the manipulation. Further, the setting function 37a may obtain a target position from the second target position database 86 by using the received type of the device, while implementing the same method as the method described above by which the target position is obtained from the second target position database 86 by using the type of the manipulation.

Further, in the fifth embodiment, the example is explained in which the second operation position database 85 has stored therein the operation positions so as to be kept in correspondence with the pieces of unique information of the practitioner, the types of target regions, and the types of manipulations, whereas the second target position database 86 has stored therein the target positions so as to be kept in correspondence with the pieces of unique information of the practitioner, the types of target regions, and the types of manipulations. However, another arrangement is acceptable in which the second operation position database 85 has stored therein operation positions so as to be kept in correspondence with at least one selected from between types of target regions (or types of the subject P) and types of manipulations (or types of devices) together with the pieces of unique information of the practitioner, whereas the second target position database 86 has stored therein target positions so as to be kept in correspondence with at least one selected from between types of target regions (or types of the subject P) and types of manipulations (or types of devices) together with the pieces of unique information of the practitioner. In that situation, by using the same method as described above, the setting function 37a obtains an operation position and a target position.

In the fifth embodiment, the second operation position database 85 and the second target position database 86 may be integrated into a single database, and the single database may be used to execute the above-described various processes. For example, a single database registered in association with the levels of body height of practitioners, the levels of body weight of practitioners, the types of dominant arms of practitioners, the types of target regions (or the types of postures of the subject P), the types of the manipulation (or the types of devices employed for the manipulations), the Z-axis values, the X-axis values and the Y-axis values of operation positions that are either obtained from simulations or statistically calculated, and the Z-axis values, the X-axis values and the Y-axis values of target positions that are either obtained from simulations or statistically calculated may be used to execute the above-described various processes.

Sixth Embodiment

Figures 24, 25:
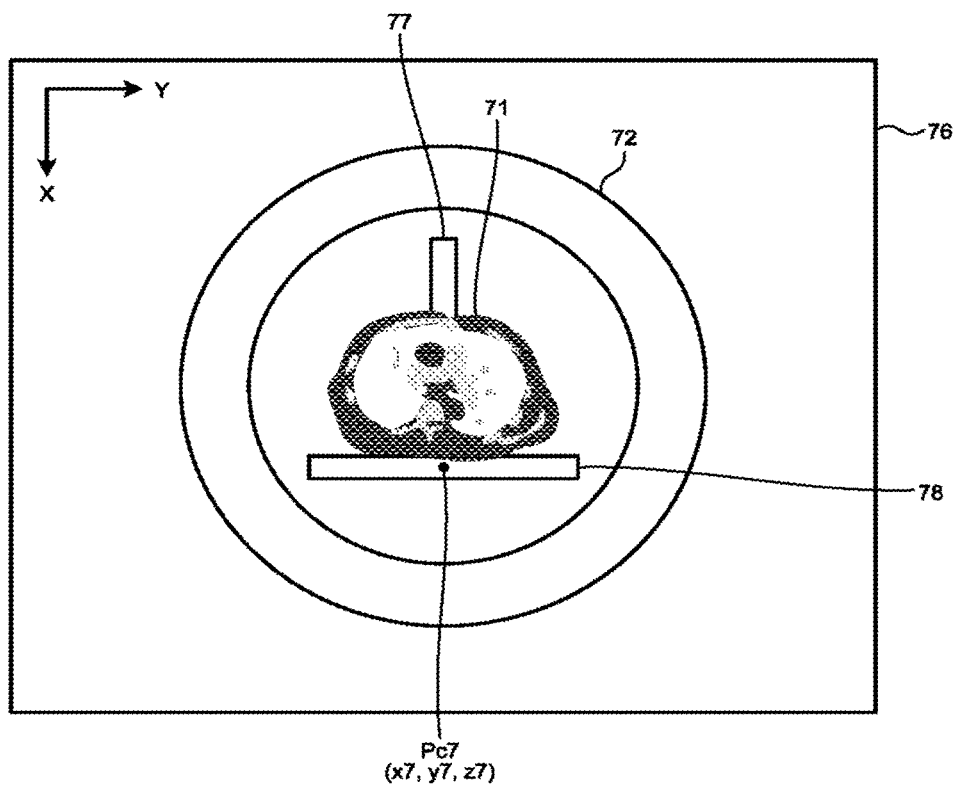
FIG. 24 is a drawing illustrating an example of a setting screen according to a sixth embodiment.
FIG. 25 is a drawing illustrating an example of a data structure of a third operation position database according to a seventh embodiment.

Next, an embodiment in which an operation position is set by using a GUI and that is different from the second embodiment will be explained as a sixth embodiment. FIG. 24 is a drawing illustrating an example of a setting screen according to the sixth embodiment. The setting function 37a according to the sixth embodiment is configured to cause the display 32 to display the setting screen 63 illustrated in FIGS. 9 and 11 explained above and a setting screen 76 illustrated in FIG. 24.

When the coronal image 62 of the subject P contained in the setting screen 63 illustrated in FIG. 9 explained above is moved in the Y-axis direction, the axial image 71, an image 77 rendering the puncture needle, and an image 78 rendering the couchtop 22 illustrated in FIG. 24 (explained later) also move in the Y-axis direction in conjunction therewith.

FIG. 24 is a drawing illustrating an example of a setting screen containing the axial image of the subject P. The setting screen 76 illustrated in FIG. 23 contains the image 72 rendering the gantry, the axial image 71 of the subject P, the image 77 rendering the puncture needle employed for the manipulation, and the image 78 rendering the couchtop 22 on which the subject P is placed. In this situation, the puncture needle is an example of the device employed for the manipulation. The image 77 is an example of the third image. The image 78 is an example of the fourth image. The axial image 71 is displayed on the setting screen 76 so as to be movable by the practitioner in conjunction with the image 77 and the image 78.

By operating the input circuitry 31, the practitioner sets the position of the axial image 71 in the X-axis direction in such a manner that the subject P contained in the axial image 71, the puncture needle indicated by the image 77, and the couchtop 22 indicated by the image 78 are not in contact with the gantry indicated by the image 72. In this situation, it is also possible to set the position of the axial image 71 in the Y-axis direction on the setting screen 76. When the axial image 71 is moved in the Y-axis direction, the coronal image 62 also moves in the Y-axis direction in conjunction therewith. Further, the setting function 37a sets a target position Pc7 (x7,y7,z7) in the real space, on the basis of the relative positional relationship or the like among the images 67 and 72 rendering the gantry, the coronal image 62 and the axial image 71 rendering the subject P.

As explained above, the processing circuitry 37 sets the predetermined position of the couchtop 22, by using the configuration in which, in the display image displayed by the display 32, a third image and a fourth image move, together with the coronal image 62 and relative to the image 67 rendering the gantry, in response to the operation, the third image rendering the device employed for the manipulation applied to the subject P and the fourth image rendering the couchtop 22.

Seventh Embodiment

Further, it is also possible to consider that the operation position is unique in correspondence with the position where the practitioner is present when performing a puncture process in addition to the physique and the dominant arm of the practitioner. For example, when the gantry 10 is viewed from the front, the operation position may be different between when the practitioner is positioned on the right side of the couch device 20 and when the practitioner is positioned on the left side of the couch device 20.

Thus, it is acceptable to use a database (a third operation position database) storing therein operation positions so as to be kept in correspondence with positions of the practitioner, in addition to the pieces of information about the physiques and the dominant arms of the practitioner (the pieces of unique information of the practitioner) and to derive an operation position suitable for the practitioner from the third operation position database.

This embodiment will be explained as a seventh embodiment.

FIG. 25 is a drawing illustrating an example of a data structure of the third operation position database according to the seventh embodiment. As illustrated by the example in FIG. 25, a third operation position database 87 includes items such as "height of practitioner", "weight of practitioner", "dominant arm of practitioner", "position of practitioner", "IN/OUT", "UP/DOWN", and "LEFT/RIGHT". The third operation position database 87 is stored in the storage circuitry 35.

The contents registered under the items "height of practitioner", "weight of practitioner" and "dominant arm of practitioner" in the third operation position database 87 are the same as the contents registered under the items "height of practitioner", "weight of practitioner", and "dominant arm of practitioner", in the first operation position database 81 illustrated in FIG. 14. Thus, the explanation thereof will be omitted.

The types of positions of the practitioner registered under the item "position of practitioner" in the third operation position database 87 are two types, namely, when the practitioner is positioned on the "right side" of the couch device 20 and when the practitioner is positioned on the "left side" of the couch device 20, as the gantry 10 is viewed from the front. In the present example, the total number of records in the third operation position database 87 is 616 (11×14× 2×2). In other words, the third operation position database 87 has registered therein all the combinations made up of the levels of height of the practitioner, the levels of weight of the practitioner, the types of dominant arms of the practitioner, and the types of positions of the practitioner.

Registered under the item "IN/OUT" are the Z-axis values of operation positions that are either obtained from simulations or statistically calculated, with respect to all the combinations made up of the levels of height of the practitioner, the levels of weight of the practitioner, the types of dominant arms of the practitioner, and the types of positions of the practitioner. In the present example in the seventh embodiment, the operation position denotes a position of the couchtop 22 where, for example, the practitioner is able to easily perform the puncture process while the subject P is not in contact with the gantry 10.

Registered under the item "UP/DOWN" are the X-axis values of operation positions that are either obtained from simulations or statistically calculated, with respect to all the combinations made up of the levels of height of the practitioner, the levels of weight of the practitioner, the types of dominant arms of the practitioner, and the types of positions of the practitioner.

Registered under the item "LEFT/RIGHT" are the Y-axis values of operation positions that are either obtained from simulations or statistically calculated, with respect to all the combinations made up of the levels of height of the practitioner, the levels of weight of the practitioner, the types of dominant arms of the practitioner, and the types of positions of the practitioner.

As explained above, the third operation position database 87 has stored therein the operation positions with respect to all the combinations made up of the levels of height of the practitioner, the levels of weight of the practitioner, the types of dominant arms of the practitioner, and the types of positions of the practitioner. In other words, the third operation position database 87 has stored therein the operation position corresponding to each of the plurality of combinations made up of the pieces of unique information of the practitioner, and the types of positions of the practitioner. Accordingly, the storage circuitry 35 has stored therein the pieces of information related to the plurality of puncture positions corresponding to the plurality of combinations made up of the pieces of unique information of the plurality of practitioners and the positions (the positions of the practitioner described above) where the plurality of practitioners are each present when applying the manipulation.

Further, the setting function 37a according to the seventh embodiment receives the unique information of the practitioner (the information related to the height, the weight, and the dominant arm of the practitioner) and the type of the position of the practitioner, from the practitioner. For example, the setting function 37a causes the display 32 to display a receiving screen used for receiving an input of the unique information of the practitioner and the type of the position of the practitioner, from the practitioner.

After that, when the "move to operation position" button 54 has been pressed by the practitioner, the setting function 37a identifies, by using the unique information of the practitioner and the type of the position of the practitioner received on the receiving screen, a record registering therein unique information of a practitioner and a type of a position of the practitioner to which the unique information of the practitioner and the type of the position of the practitioner received on the receiving screen are most similar, from among all the records in the third operation position database 87. After that, the setting function 37a obtains the operation position registered in the identified record.

After that, the couchtop controlling function 37b according to the seventh embodiment transmits an instruction to move the couchtop 22 to the operation position obtained by the setting function 37a, to the scan controlling circuitry 33. In other words, when the first practitioner is to apply the manipulation while being present in a first position, the processing circuitry 37 controls the couch driving device 21 so as to move the couchtop 22 to the puncture position indicated by a piece of information related to the puncture position corresponding to the unique information of the first practitioner and the first position where the first practitioner is present when applying the manipulation, the piece of information being among the pieces of information that are related to the plurality of puncture positions and are stored in the storage circuitry 35. Accordingly, the couchtop 22 is moved to the operation position suitable for the physique, the dominant arm, and the position of the practitioner. In other words, the couchtop controlling function 37b moves the couchtop 22 to the operation position corresponding to the unique information and the position of the practitioner. Consequently, it is possible to move the subject P to the position where the practitioner is able to easily perform the puncture process, while the subject P is not in contact with the gantry 10.

The seventh embodiment has thus been explained. According to the seventh embodiment, it is possible to move the subject P to the position where the practitioner is able to easily perform the puncture process, similar to the first embodiment.

Eighth Embodiment

An eighth embodiment will be described. For example, in the eighth embodiment, a single database (a fourth database) registered in association with the levels of body height of practitioners, the levels of body weight of practitioners, the types of dominant arms of practitioners, the types of positions of the practitioner, the levels of body height of subjects P, the levels of body height of subjects P, the types of target regions (or the types of postures of the subject P), the types of the manipulation (or the types of devices employed for the manipulations), the Z-axis values, the X-axis values and the Y-axis values of operation positions that are either obtained from simulations or statistically calculated, and the Z-axis values, the X-axis values and the Y-axis values of target positions that are either obtained from simulations or statistically calculated is stored in the storage circuitry 35.

Further, the setting function 37a according to the eighth embodiment receives the unique information of the practitioner (the information related to the height, the weight, and the dominant arm of the practitioner), the type of the position of the practitioner, the unique information of the subjects P (the information related to the height, and the weight of the subjects P), the types of target regions (or the types of postures of the subject P), and the types of the manipulation (or the types of devices employed for the manipulations) from the practitioner. For example, the setting function 37a causes the display 32 to display a receiving screen used for receiving an input of the unique information of the practitioner, the type of the position of the practitioner, the unique information of the subjects P, the types of target regions (or the types of postures of the subject P), and the types of the manipulation (or the types of devices employed for the manipulations) from the practitioner.

After that, when the "move to operation position" button 54 has been pressed by the practitioner, the setting function 37a identifies, by using the unique information of the practitioner, the type of the position of the practitioner, the unique information of the subjects P, the types of target regions (or the types of postures of the subject P), and the types of the manipulation (or the types of devices employed for the manipulations) received on the receiving screen, a record registering therein unique information of a practitioner, a type of a position of the practitioner, unique information of a subjects P, a type of target region (or a type of posture of the subject P), and a type of a manipulation (or a type of device employed for the manipulation) to which the unique information of the practitioner, the type of the position of the practitioner, unique information of the subjects P, the type of target region (or the type of posture of the subject P), and the type of the manipulation (or the type of device employed for the manipulation) received on the receiving screen are most similar, from among all the records in the fourth database. After that, the setting function 37a obtains the operation position registered in the identified record.

After that, the couchtop controlling function 37b according to the eighth embodiment transmits an instruction to move the couchtop 22 to the operation position obtained by the setting function 37a, to the scan controlling circuitry 33. Accordingly, the couchtop 22 is moved to the operation position suitable for the physique, the dominant arm, and the position of the practitioner, the physique, the target region (or the posture) of the subject P, and the manipulation (or the device). In other words, the couchtop controlling function 37b moves the couchtop 22 to the operation position corresponding to the physique, the dominant arm, and the position of the practitioner, the physique, the target region (or the posture) of the subject P, and the manipulation (or the device). Consequently, it is possible to move the subject P to the position where the practitioner is able to easily perform the puncture process, while the subject P is not in contact with the gantry 10.

After that, when the "move to target position" button 44 has been pressed by the practitioner, the setting function 37a identifies, by using the unique information of the practitioner, the type of the position of the practitioner, the unique information of the subjects P, the types of target regions (or the types of postures of the subject P), and the types of the manipulation (or the types of devices employed for the manipulations) received on the receiving screen, a record registering therein unique information of a practitioner, a type of a position of the practitioner, unique information of a subjects P, a type of target region (or a type of posture of the subject P), and a type of a manipulation (or a type of device employed for the manipulation) to which the unique information of the practitioner, the type of the position of the practitioner, unique information of the subjects P, the type of target region (or the type of posture of the subject P), and the type of the manipulation (or the type of device employed for the manipulation) received on the receiving screen are most similar, from among all the records in the fourth database. After that, the setting function 37a obtains the target position registered in the identified record.

After that, the couchtop controlling function 37b according to the eighth embodiment transmits an instruction to move the couchtop 22 to the target position obtained by the setting function 37a, to the scan controlling circuitry 33. Accordingly, the couchtop 22 is moved to the target position suitable for the physique, the dominant arm, and the position of the practitioner, the physique, the target region (or the posture) of the subject P, and the manipulation (or the device). In other words, the couchtop controlling function 37b moves the couchtop 22 to the target position corresponding to the physique, the dominant arm, and the position of the practitioner, the physique, the target region (or the posture) of the subject P, and the manipulation (or the device). Consequently, it is possible to move the subject P to the position where it is possible to image the puncture target site and the puncture needle rendered in the X-ray CT image, while the subject P is not in contact with the gantry 10.

The eighth embodiment has thus been explained. According to the eighth embodiment, it is possible to move the subject P to the position where the practitioner is able to easily perform the puncture process, similarly to the first embodiment.

In the eighth embodiment, one or more of the eight pieces of the levels of body height of practitioners, the levels of body weight of practitioners, the types of dominant arms of practitioners, the types of positions of the practitioner, the levels of body height of subjects P, the levels of body height of subjects P, the types of target regions (or the types of postures of the subject P), and the types of the manipulation (or the types of devices employed for the manipulations) registered in the fourth database may be omitted. In this case, a type of information accepted from practitioners by the setting function 37a is the same as a type of information registered in the fourth database.

According to at least one aspect of the embodiments of the X-ray CT apparatus described above, it is possible to move the subject P to the position where the practitioner is able to easily perform the puncture process.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT apparatus comprising:
   a gantry having an opening provided to be interposed between an X-ray tube and an X-ray detector;
   a couch including driving circuitry configured to insert a couchtop on which a subject is placed, into the opening;
   storage circuitry configured to store therein pieces of information that are related to a plurality of puncture positions of the couchtop and that correspond to pieces of unique information of a plurality of practitioners who each apply a manipulation to the subject, each of the pieces of unique information comprising at least one of a piece of information indicating a physique of each of the plurality of practitioners, a piece of information indicating a dominant arm of each of the plurality of practitioners, and a piece of information indicating which side of the couch each of the plurality of practitioners is positioned; and
   processing circuitry configured, when a first practitioner is to apply the manipulation, to control the driving circuitry so as to move the couchtop to a puncture position indicated by a piece of information related to a puncture position corresponding to a piece of unique information pertaining to the first practitioner, the piece of information being among the pieces of information that are related to the plurality of puncture positions and are stored in the storage circuitry.

2. The X-ray CT apparatus according to claim 1, wherein the processing circuitry obtains a first piece of unique information of the first practitioner, and
   on a basis of the first piece of unique information, the processing circuitry controls the driving circuitry so as to move the couchtop to the puncture position indicated by the piece of information related to the puncture position corresponding to the piece of unique information which is similar to the first piece of unique information, the piece of information being among the pieces of information that are related to the plurality of puncture positions and are stored in the storage circuitry.

3. The X-ray CT apparatus according to claim 1, wherein the storage circuitry stores therein the pieces of information that are related to the plurality of puncture positions and that correspond to a piece of unique information of the subject for each of pieces of unique information of a plurality of subjects, and
   the processing circuitry controls the driving circuitry so as to move the couchtop to the puncture position indicated by the piece of information related to the puncture position corresponding to a piece of unique information of a practitioner, which is similar to the piece of unique information of the first practitioner, and a piece of unique information of a subject, which is similar to a piece of unique information of a first subject to whom the manipulation is applied by the first practitioner, the piece of information being among the pieces of information that are related to the plurality of puncture positions and are stored in the storage circuitry.

4. The X-ray CT apparatus according to claim 1, wherein the storage circuitry stores therein pieces of information that are related to a plurality of image taking positions and that correspond to a plurality of combinations made up of the pieces of unique information of the plurality of practitioners and pieces of unique information of a plurality of subjects, and
   the processing circuitry controls the driving circuitry so as to move the couchtop to the puncture position indicated by a piece of information related to an image taking position corresponding to the piece of unique information of the first practitioner and a piece of unique information of a first subject to whom the manipulation is applied by the first practitioner, the piece of information being among the pieces of information that are related to the plurality of image taking positions and are stored in the storage circuitry.

5. The X-ray CT apparatus according to claim 1, wherein the storage circuitry stores therein the pieces of information that are related to the plurality of puncture positions and that correspond to a plurality of combinations made up of the pieces of unique information of the plurality of practitioners, target regions of the subject, and the manipulations applied to the subject, and
   the processing circuitry controls the driving circuitry so as to move the couchtop to the puncture position indicated by the piece of information related to the puncture position corresponding to the piece of unique information of the first practitioner, a first target region of a first subject to whom a first manipulation is applied by the first practitioner, and the first manipulation, the piece of information being among the pieces of information that are related to the plurality of puncture positions and are stored in the storage circuitry.

6. The X-ray CT apparatus according to claim 1, wherein the storage circuitry stores therein pieces of information that are related to a plurality of image taking positions and that correspond to a plurality of combinations made up of the pieces of unique information of the plurality of practitioners, target regions of the subject, and the manipulations applied to the subject, and the processing circuitry controls the driving circuitry so as to move the couchtop to an image taking position indicated by a piece of information related to an image taking position corresponding to the piece of unique information of the first practitioner, a first target region of a first subject to whom a first manipulation is applied by the first practitioner, and the first manipulation, the piece of information being among the pieces of information that are related to the plurality of image taking positions and are stored in the storage circuitry.

7. The X-ray CT apparatus according to claim 1, wherein the storage circuitry stores therein pieces of information that are related to the plurality of puncture positions and that correspond to a plurality of combinations made up of the pieces of unique information of the plurality of practitioners and positions where the plurality of practitioners are each present when applying the manipulation, and when the first practitioner is to apply the manipulation while being present in a first position, the processing circuitry controls the driving circuitry so as to move the couchtop to the puncture position indicated by a piece of information related to a puncture position corresponding to the piece of unique information of the first practitioner and the first position where the first practitioner is present when applying the manipulation, the piece of information being among the pieces of information that are related to the plurality of puncture positions and are stored in the storage circuitry.

8. An X-ray CT apparatus comprising:
a gantry having an opening provided to be interposed between an X-ray tube and an X-ray detector;
a couch including driving circuitry configured to insert a couchtop on which a subject is placed, into the opening; and
processing circuitry configured to estimate a position of the subject in a real space based on a position of a second image relative to a first image rendering the gantry on a display screen of a display in which the second image is movable relative to the first image in response to an operation, and set a predetermined position of the couchtop based on the estimated position, the second image containing a puncture target site of the subject.

9. The X-ray CT apparatus according to claim 8, wherein the processing circuitry causes the display to display at least one of a median line of the opening and a figure indicating a moveable range of the couchtop, together with the first image and the second image.

10. The X-ray CT apparatus according to claim 8, wherein the processing circuitry sets the predetermined position of the couchtop by using a configuration in which, in a display image displayed by the display, a third image and a fourth image move, together with the second image and relative to the first image, in response to an operation, the third image rendering a device employed for a manipulation applied to the subject and the fourth image rendering the couchtop.

11. The X-ray CT apparatus according to claim 10, wherein the processing circuitry further estimates a site of the subject that is positioned within the opening and causes the display to display a fifth image containing the estimated site and the first image.

* * * * *